United States Patent
Blotsky et al.

(10) Patent No.: US 11,746,067 B2
(45) Date of Patent: *Sep. 5, 2023

(54) METHODS AND COMPOSITIONS FOR TREATING SOIL AND PLANTS

(71) Applicant: Core Intellectual Properties Holdings, LLC, Goodyear, AZ (US)

(72) Inventors: Luke Blotsky, Goodyear, AZ (US); Karin L. Hastings, Goodyear, AZ (US); Derex Q. Zellars, Goodyear, AZ (US)

(73) Assignee: Core Intellectual Properties Holdings, LLC, Goodyear, AZ (US)

( * ) Notice: Subject to any disclaimer, the term of this patent is extended or adjusted under 35 U.S.C. 154(b) by 885 days.

This patent is subject to a terminal disclaimer.

(21) Appl. No.: 16/667,045

(22) Filed: Oct. 29, 2019

(65) Prior Publication Data

US 2020/0079701 A1    Mar. 12, 2020

Related U.S. Application Data

(63) Continuation of application No. 15/235,536, filed on Aug. 12, 2016, now Pat. No. 10,457,610, which is a continuation of application No. 14/033,339, filed on Sep. 20, 2013, now Pat. No. 9,428,425.

(60) Provisional application No. 61/703,644, filed on Sep. 20, 2012.

(51) Int. Cl.
| | | |
|---|---|---|
| C05F 11/00 | (2006.01) | |
| C11D 7/40 | (2006.01) | |
| C05F 11/08 | (2006.01) | |
| C12N 1/12 | (2006.01) | |

(52) U.S. Cl.
CPC ............. *C05F 11/00* (2013.01); *C05F 11/08* (2013.01); *C11D 7/40* (2013.01); *C12N 1/12* (2013.01)

(58) Field of Classification Search
None
See application file for complete search history.

(56) References Cited

U.S. PATENT DOCUMENTS

| | | |
|---|---|---|
| 3,617,215 A | 11/1971 | Sugahara et al. |
| 3,645,040 A | 2/1972 | Ort |
| 3,969,844 A | 7/1976 | Fogel et al. |
| 4,533,459 A | 8/1985 | Dente et al. |
| 4,675,114 A | 6/1987 | Zagyvai et al. |
| 4,774,186 A | 9/1988 | Schaefer, Jr. et al. |
| 4,904,627 A | 2/1990 | Bhattacharyya |
| 4,919,702 A | 4/1990 | Weitzien et al. |
| 5,241,296 A | 8/1993 | Naka et al. |
| 5,527,783 A | 6/1996 | Derrieu et al. |
| 5,554,576 A | 9/1996 | Mookerjee et al. |
| 5,950,361 A | 9/1999 | Takamatsu et al. |
| 6,083,293 A | 7/2000 | Bath |
| 6,100,092 A | 8/2000 | Borysiyuk et al. |
| 6,207,882 B1 | 3/2001 | Ding |
| 6,355,860 B1 | 3/2002 | Borysiyuk et al. |
| 6,602,500 B1 * | 8/2003 | Kharbanda ............ C07K 14/32 424/93.46 |
| 6,849,576 B2 | 2/2005 | Suzuki et al. |
| 6,884,759 B2 | 4/2005 | Hayashi et al. |
| 6,896,883 B2 | 5/2005 | Bergstrom et al. |
| 6,987,130 B1 | 1/2006 | Yokoyama et al. |
| 7,074,565 B2 | 7/2006 | Dunbar |
| 8,122,637 B2 | 2/2012 | Blotsky |
| 8,574,887 B2 | 11/2013 | Stepenoff et al. |
| 8,709,497 B2 | 4/2014 | Blotsky et al. |
| 8,722,389 B1 | 5/2014 | Das et al. |
| 8,927,031 B2 | 1/2015 | Blotsky et al. |
| 9,044,417 B2 | 6/2015 | Blotsky et al. |
| 9,107,869 B2 | 8/2015 | Blotsky et al. |
| 9,113,605 B2 | 8/2015 | Hastings |
| 9,180,141 B1 | 11/2015 | Blotsky et al. |
| 9,241,955 B2 | 1/2016 | Blotsky et al. |
| 9,428,425 B2 | 8/2016 | Blotsky et al. |
| 9,504,713 B2 | 11/2016 | Blotsky et al. |
| 9,549,565 B2 | 1/2017 | Wilborn et al. |
| 9,737,572 B2 | 8/2017 | Blotsky et al. |
| 9,999,239 B2 | 6/2018 | Blotsky et al. |
| 10,006,001 B2 | 6/2018 | Hastings |
| 10,016,450 B2 | 7/2018 | Blotsky et al. |
| 10,034,904 B2 | 7/2018 | Blotsky et al. |
| 10,406,176 B2 | 9/2019 | Blotsky et al. |
| 10,457,610 B2 | 10/2019 | Blotsky et al. |
| 10,603,343 B2 | 3/2020 | Blotsky et al. |
| 2002/0069685 A1 | 6/2002 | Adam |

(Continued)

FOREIGN PATENT DOCUMENTS

WO    2012067674 A1    5/2012

OTHER PUBLICATIONS

Nannochloropsis, NCBI Taxonomy Database, 2022, https://www.ncbi.nlm.nih.gov/Taxonomy/Browser/wwwtax.cgi?mode=Info&id=5748&lvl=3&lin=f&keep=1&srchmode=1&unlock (Year: 2022).*

Nannochloris, NCBI Taxonomy Database, 2022, https://www.ncbi.nlm.nih.gov/Taxonomy/Browser/wwwtax.cgi?mode=Info&id=3187&lvl=3&lin=f&keep=1&srchmode=1&unlock (Year: 2022).*

Abu. G.O. et al., Optimization studies of biomass production and protein biosynthesis in a *Spirulina* sp. isolated from an oil-polluted flame pit in the Niger Delta, Afr, J. Biotechnol. 6: 2550-2554 (2007).

Beakes, G. et al., Zoospores ultrastructure of Zygorhizidium affluens and Z. planktonicum, two chytrids parasitizing the diatom Asterionella formosa, Can J. Bot. 66: 1054-1067 (1988).

(Continued)

*Primary Examiner* — Louise W Humphrey
*Assistant Examiner* — Trevor L Kane
(74) *Attorney, Agent, or Firm* — Noblitt & Newson, PLLC

(57) ABSTRACT

The present invention comprises methods and compositions comprising a microalgae consortium. A composition comprises at least one genera of microalgae flocculated by *Paenibacillus polymyxa* strain, Strain 2, deposited under the Budapest Treaty as ATCC Accession No. PTA-12841. Methods of treating the soil comprise adding a composition of the present invention to soil.

19 Claims, 7 Drawing Sheets

(56) References Cited

U.S. PATENT DOCUMENTS

| | | |
|---|---|---|
| 2004/0258597 A1 | 12/2004 | Michalakos et al. |
| 2005/0118279 A1 | 6/2005 | Blotsky et al. |
| 2007/0031462 A1 | 2/2007 | Blotsky et al. |
| 2007/0190173 A1 | 8/2007 | Blotsky et al. |
| 2009/0226545 A1 | 9/2009 | Blotsky et al. |
| 2009/0227003 A1 | 9/2009 | Blotsky et al. |
| 2010/0092442 A1 | 4/2010 | Jacobsen et al. |
| 2010/0129465 A1 | 5/2010 | Blotsky et al. |
| 2010/0242355 A1 | 9/2010 | Blotsky |
| 2011/0124089 A1 | 5/2011 | Stepenoff et al. |
| 2011/0253623 A1 | 10/2011 | Hastings |
| 2013/0205850 A1 | 8/2013 | Ganuza |
| 2014/0030228 A1 | 1/2014 | Blotsky et al. |
| 2014/0090431 A1 | 4/2014 | Blotsky et al. |
| 2014/0314683 A1 | 10/2014 | Blotsky et al. |
| 2015/0150909 A1 | 6/2015 | Blotsky et al. |
| 2015/0250817 A1 | 9/2015 | Blotsky et al. |
| 2016/0015056 A1 | 1/2016 | Wilborn et al. |
| 2016/0015747 A1 | 1/2016 | Blotsky et al. |
| 2016/0032237 A1 | 2/2016 | Hastings |
| 2016/0199404 A1 | 7/2016 | Blotsky et al. |
| 2017/0066697 A1 | 3/2017 | Blotsky et al. |
| 2017/0119708 A1 | 5/2017 | Blotsky et al. |
| 2017/0136050 A1 | 5/2017 | Blotsky et al. |
| 2017/0202245 A1 | 7/2017 | Blotsky et al. |
| 2017/0319635 A1 | 11/2017 | Blotsky et al. |
| 2019/0175664 A1 | 6/2019 | Blotsky et al. |
| 2020/0038435 A1 | 2/2020 | Blotsky et al. |
| 2020/0079701 A1 | 3/2020 | Blotsky et al. |
| 2020/0222471 A1 | 7/2020 | Blotsky et al. |

OTHER PUBLICATIONS

Berard, A. et al. Pollution-induced community tolerance (PICT and seasonal variations in the sensitivity of phytoplankton to atrazine in nanocosms, Chemosphere 45: 427-437 (2001).

Berard, A. et al. Tolerance of Oscillatoria limnetica Lemmermann to atrazine in natural phytoplankton populations and in pure culture: Influence of Season and Temperature, ARch. Environ. Con. Tox. 37: 472-479 (1999).

Bold, H.C., The morphology of Chamydomonas chlamydogama sp. nov. Bull. Torrey Bot. Club. 76: 101-108 (1949).

Bot, A. et al. The inmportance of soil organic matter: key to drought-resistant soil and sustained food production. FAO Soils Bulletin 80: 95 pages (2005).

Brock T.D. Primary colonization of Surtsey, with special reference to the blue-green algae. Oikos 24: 237-243 (1973).

Doherty, S.M. et al., Biological criteria for inland freshwater wetlands in Florida: a review of technical and scientific literature (1990-1999). Report to the United States Environmental Protection Agency, Center for Wetlands, University of Florida, Gainesville, FL Dec. 2000.

Fujita, Y. et al. Effects of cultivation conditions on algal communities in paddy soils, Jap. J. Limnol. 60: 77-86 (1999).

Gong et al. Culture Conditions for Flocculant Production by Paenbacillus polymyxa BY-28, Journal of Environmental Science and Health, Part A. vol. A38, No. 4. pp. 657-669 (2003).

Hargrove, W.W. et al. A New High-Resolution National Map of Vegitation Ecoregions Produced Empirically Using Multivariate Spatial Clustering. Available at http://www.geobabble.org/~hnw/esri98/ (10 pages (1988).

Helfrich et al., Clearing Muddy Pond Waters, Virginia Cooperative Extension, (2 pages) (2009).

Kryder L.R. Microalgae for Wastwater Treatment and Reuse. Available at http://www.leslieconsulting.com/docs/MicroalgaeForWastwaterTreatmentAndReuse.pdf. (10 pages) (2007).

Lee et al. Microbial flocculation, a potentially low-cost harvesting technique for marine microalgae for the production of biodiesel, J. Appl. Phycol, 21: 559-567 (2008).

Lee SJ et al., (1998) Effects of harvesting method and growth stage on the flocculation of the green alga Botryococcus braunii. Letters Applied Microbiology. 27: 14-18.

Lukesova, Soil algae in four secondary successional stages on abandoned fields. Algological Stud. 71: 81102 (1993).

Malakar, E. et al., A perspective towards development and commercialization of potential bga biofertilizers of Assam, North East India and carrier materials for BGA mass production and Inoculum development. Annals of Biological Research (2012) 3 (1): 814-828.

Metting B. et al., (1983) The Influence of a Microalgal Conditioner on Selected Washington Soils: An Empirical Study. Soil Sci. Soc. Am. J. 14:682-685.

Neustupa, J., Soil algae from marlstone-substratum based biotopes in the Nature park Dzvba'n (Central Bohemia, Czech Republic) with special attention to the natural treeless localities. Algological Stud. 101: 109-120 (2001).

Oh et al., Harvesting of Chiarella vulgariz using bioflocculant from Paenibacillus sp. AM49, Biotechnology Letters 23: 1229-1234 (2001).

Oh HM et al., (2001) Harvesting of Chlorella vulgaris using a bioflocculant form Paenibacillus sp. AM49. Biotechnology Letters. 23: 1229-1234.

Pandey, J.P. et al., Optimization of biomass production of Spirulina maxima J. Algal Biomass Utilization. 1: 20-32 (2010).

Pankhurst, C. et al., Biological Indicators of Soil Health, CAB International, London (40 pages (1997).

Paoletti, M.G., Soil invertebrates in cultivated and uncultivated soils in North-East Italy. Redia 71: 501-563 (1988).

Poelman E. et al., (1997) Potential of electrolytic flocculation for recovery of micro-algae. Resources, Conservation and Recycling. 19(1): 1-10. (Abstract only).

Shelef et al., Microalgae Harvesting and Processing: A literature Review, Solar Energy Research Institute (71 pages) (1984).

Stanier R.Y. et al., Purification and properties of unicellular bluegreen algae (Order: Chroococcales). Bacteriological Reviews. 35: 171-205 (1971).

Suh HH, et al., (1998) Production and Rheological Properties of Bioflocculant Produced by Bacillus sp. DP-152. J. Microbiol. Biotechnol. 8(6): 618-624.

Thirup, L. et al., Population dynamics of the fast-growing subpopulations of Pseudmonas and total bacteria, and their protozoan grazers, revealed by fenpropimorph treatment, Soil. Biol. Biochem. 32: 1615-1623 (2000).

Tsujimura, S. et al., Estimation of soil algal biomass in salinized irrigation land: a comparison of culture dilution and chlorophyll a extraction methods, J. Appl. Phycol. 12: 1-8 (2000).

Yang et al., Culture Medium and Grading Culture Technics for Bioflocculant Production by Paenbacillus polymyxa GA 1, Environmental Science, vol. 27, No. 7, (2006).

Yeates, G.W. et al., Feeding habits in soil nematodes families and genera: an outline for soil ecologists. J. Nematol. 25: 315-331 (1993).

Yoon, J.H. et al., Paenibacillus kribbensis sp. nov. and Paenibacillus terrae sp. nov., bioflocculants for efficient harvesting of algal cells. International Journal of Systematic and Evolutionary Microbiology. 53: 295-301 (2003).

* cited by examiner

METHODS AND COMPOSITIONS FOR TREATING SOIL AND PLANTS

RELATED APPLICATIONS

This application is a continuation application of U.S. patent application Ser. No. 15/235,536, filed Aug. 12, 2016, now U.S. Pat. No. 10,457,610, issued on Oct. 29, 2019, which is a continuation application of U.S. patent application Ser. No. 14/033,339, filed Sep. 20, 2013, now U.S. Pat. No. 9,428,425, issued on Aug. 30, 2016, which claims the priority of and the benefit of the filing date of U.S. Provisional Patent Application Ser. No. 61/703,644, filed Sep. 20, 2012, all of which are incorporated by reference herein.

TECHNICAL AREA

The present invention comprises methods and compositions for treating soil and plants, particularly comprising compositions comprising a microalgae consortium.

BACKGROUND

Long use of chemical fertilizers and pesticides is known to deplete soil of beneficial organisms and leads to lower soil quality. Plants grown in such soils do not grow at the optimum rate or mass and yields are lower. Additionally, such plants may be at higher risk of infection and have lower immune-type responses to pests.

The size and activity of soil microbial communities are indicators of soil health, quality and fertility necessary for sustainable agriculture (Doran and Parkin, 1994; Kennedy and Papendick, 1995; Warkentin, 1995; Sparling, 1997). These communities have been classified into eubacteria, cyanobacteria, actinomycetes, archaebacteria, fungi, microalgae, protozoa, viruses, and some nematodes (Paul and Clark, 1989; Sims, 1990; Roper and Gupta, 1995). Out of these groups, microalgae perform several important functions for agro-ecosystems and can also function as a bio indicator for soil quality.

What is needed are methods and compositions comprising microalgae that can be used for treating or amending soil.

SUMMARY

The present invention comprises methods and compositions for treating soil, comprising a consortium, or combination, of microalgae. Methods of the present invention comprise methods for treating or amending soil, methods for combining the microalgae compositions with other compositions that are beneficial for treating soil, and methods for combining microalgae species to form a microalgae composition of the present invention. Methods for cleaning or maintaining irrigation equipment are disclosed. Compositions of the present invention comprise a microalgae composition comprising at least one microalgae, and compositions comprising a microalgae composition of the present invention admixed with other compositions beneficial for soil.

DESCRIPTION OF FIGURES

FIG. 1A. Soil with pH<8.0, FIG. 1B. Soil with pH>8.0

FIG. 2A. Areas with pH<8.0, FIG. 2B. Areas with pH>8.0.

FIG. 3A. Total counts all plots pre-treatment. FIG. 3B. Control pre-treatment. FIG. 3C. Total counts all plots pH<8.0. FIG. 3D. Control pH<8.0. FIG. 3E. Total counts all plots pH>8.0. FIG. 3F. Control pH>8.0 FIG. 3G. Total counts all plots 2 months after harvest. FIG. 3H. Control 2 months after harvest.

FIG. 4A. Comparison of pH values observed at harvest and two months post-harvest in soils with pH<8.0 FIG. 4B. Comparison of pH values observed at harvest and two months post-harvest in soils with pH<8.0.

DETAILED DESCRIPTION

Figure 1A:
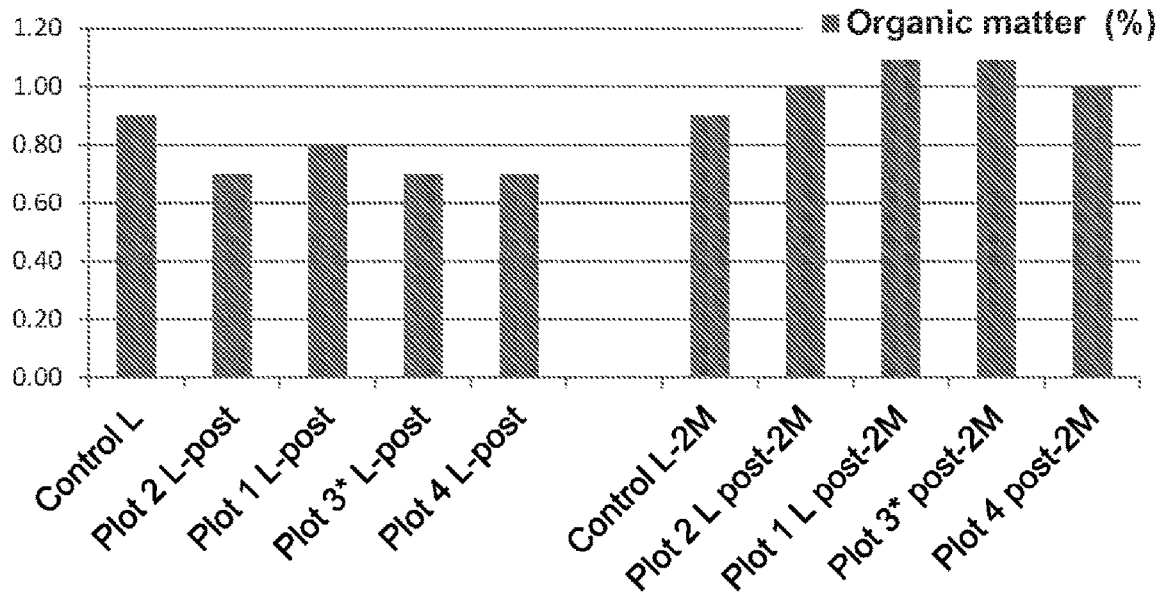
FIGS. 1A and 1B show graphs of differences in percent organic matter (OM) before and after treatment with a microalgae consortium composition of the present invention.

The present invention comprises methods and compositions comprising microalgae. Microalgae are found in nearly all soil environments, from desert sand, to the tundra. Microalgae remove and process excess nutrients such as carbon, nitrogen, and phosphorus in water and soil. They then excrete more metabolically accessible forms of these nutrients for plants. Microalgae provide important polysaccharides, lipids (fatty acids), proteins and hydrocarbons to the soil to add to its structure. Microalgae provide enzymes that catalyze important reactions for plant and soil metabolic processes. It is estimated that between 1,000 and 1,000,000 microalgae cells are present in 1 gram (the weight of a paper clip) of fertile temperate soil. Over farmed soils may have depleted microalgae populations because of herbicide, fungicide, algicide, strong acid, and synthetic fertilizer usage.

The size and activity of soil microbial communities is an indicator of soil health, quality and fertility necessary for sustainable agriculture (Doran and Parkin, 1994; Kennedy and Papendick, 1995; Warkentin, 1995; Sparling, 1997). These communities have been classified into eubacteria, cyanobacteria, actinomycetes, archaebacteria, fungi, microalgae, protozoa, viruses, and some nematodes (Paul and Clark, 1989; Sims, 1990; Roper and Gupta, 1995). Out of these groups, microalgae perform several important functions for agro-ecosystems and can also function as a bio indicator for soil quality.

Four different types of microalgae are recognized in soil: green (chlorophyta), blue-green (cyanobacteria), yellow-green (xanthophyta), and diatoms (bacillariophyta) (Paul and Clark, 1989). Soil microalgae are photoautotrophs. These species do not depend on the organic matter (carbon content) of the soil and play a role as primary colonizers. They produce large amounts of secreted polysaccharides that promote soil aggregation at the surface and they are capable of nitrogen fixation. Soil habitats are the most important non-aqueous ecosystems for microalgae (Zenova et al., 1995) where these organisms contribute to soil formation and stability (Metting, 1981). In addition, microalgae contribute to energy and matter flux (Kuzyakhmetov, 1998)

and nitrogen fixation (Goyal, 1997). Green and blue-green populations in upper topsoil can perform valuable services for soil ecosystems (Metting, 1981; Starks et al., 1981) and agriculture (Ruble and Davis, 1988). One of the major benefits of microalgae is the generation of organic matter from inorganic substances (Alexander, 1977). In addition to provide a food source for other microorganisms, nematodes and invertebrates, microalgae produce biologically active compounds that can affect other components of soil communities, including plants (Metting, 1981; Zenova et al., 1995).

Methods for Amending Soil

The present invention comprises methods for amending soil, comprising providing a composition of the present invention comprising a microalgae consortium to soil. A microalgae consortium composition may be added to a solution that is applied to soil, for example, a composition of microalgae may be added to irrigation water that is applied to soil. A composition comprising a microalgae consortium composition of the present invention may be applied directly to soil in an undiluted form. A concentration of the total amount of microalgae may be $30 \times 10^6$ cells/fluid oz. which may be an undiluted form. A microalgae consortium composition may be provided in a container comprising a total amount of microalgae present in a concentration of at least $30 \times 10^6$ cells/fluid oz. and the contents of the container may be added to a larger water container or into an irrigation system water supply to then be provided to the soil. Though not required, the present invention comprises algae that are grown under certified organic conditions and are found in OMRI certified products.

A microalgae consortium composition of the present invention may be provided to soil, for example, in irrigation water, before seed is planted in the soil, after seed is planted, after plants emerge, and at any point during the life of the plant.

An aspect of the present invention comprises providing a microalgae consortium composition to soil. A microalgae consortium composition of the present invention may treat the soil by increasing the buffering capacity (CEC) of the soil, solubilizing sodium, increasing soil aggregation, and/or increasing the diversity of soil microorganisms. A microalgae consortium composition of the present invention may enhance plant growth in soils treated with a microalgae consortium composition of the present invention by increasing the accessibility of carbon, nitrogen and phosphorous and/or by reducing plant sodium stress. A microalgae consortium composition of the present invention may enhance the water provided to treated soil or plants, by providing a microalgae consortium composition of the present invention in irrigation water supplied to the soil and/or plants wherein the microalgae consortium composition helps clear the irrigation system of precipates adhering to the irrigation equipment and a microalgae consortium composition may enhance water retention in the soil treated with the microalgae consortium composition.

Though not wishing to be bound by any particular theory, it is believed that a microalgae consortium composition of the present invention increases bioavailability of nutrients to plants by the microalgae processing nutrients such as carbon, nitrogen and phosphorous to make them more accessible to the plant. A microalgae consortium composition of the present invention may reduce sodium stress on plants because the microalgae contain enzymes that solubilize salt, which helps decrease the uptake of sodium by plants. A microalgae consortium composition of the present invention may increase soil aggregation by adding cellulose and polysaccharides and build soil humus. A microalgae consortium composition of the present invention may increase the buffering capacity of soil through the addition, by the microalgae, of biochemical and enzymes so other microorganisms can function effectively and biochemical reactions are favored. A microalgae consortium composition of the present invention may clear irrigation systems of carbonates, salts and blue-green algae by microalgae enzymes and other biochemical processes. A microalgae consortium composition of the present invention may increase soil microorganism number and diversity, not only because the microalgae consortium composition itself adds its concentration of microalgae, but because the environment is enhanced by the presence and activities of the microalgae which causes other soil microorganisms to thrive in the enhanced soil environment. A microalgae consortium composition of the present invention may decrease the number of cyanobacteria or filamentous algae in the soil and/or irrigation system.

A method of treating soil or providing a soil additive of the present invention may comprise applying a microalgae consortium composition comprising a microalgae composition of $30 \times 10^6$ microalgae per fluid ounce in 1 quart to 4 quart applications per acre per crop per cycle. A composition comprising $30 \times 10^6$ microalgae per fluid ounce may be applied to the soil directly or diluted, in a range of from 1:50, from 1:40, from 1:30, from 1:20, from 1:10, from 1:5, from 1:1, and all ranges thereinbetween. The delivery mode may be any known to those skilled in the art, including, but not limited to drip, pivot or sprinkler irrigation systems. Compositions of the present invention may be applied by furrow or flat irrigation by adding a standard concentration, such as $30 \times 10^6$ microalgae per fluid ounce, to any reasonably sized water vessel, such as up to 500 gallons, and trickling into the irrigation system.

It is recommended that microalgae consortium compositions of the present invention not be applied concurrently with algaecide or herbicide. Additionally, a microalgae consortium composition of the present invention should not be applied concurrently with strong acids, for example hydrochloric or phosphoric acids, or with strongly alkaline products. The microalgae consortium compositions of the present invention may or may not be applied with other fertilizer or soil amendments.

Methods for Cleaning Irrigation Equipment

The present invention comprises methods for cleaning irrigation equipment, comprising providing a composition of the present invention comprising a microalgae consortium in the fluid pumped through the irrigation equipment. A microalgae consortium composition of the present invention traverses irrigation equipment, and causes the equipment to have less scale formation and loosens scale already formed on the irrigation equipment. For example, irrigation equipment in drip and pivot irrigation systems which distribute a microalgae consortium composition through the system has less precipitates or scale on the equipment. Usually such systems have to be cleaned periodically with phosphoric acid to remove the scale, and then residual phosphoric acid is distributed to the plants being irrigated, which is harmful for the plants.

The Present Invention Comprises Microalgae Compositions.

A microalgae consortium composition of the present invention comprises at least one of the following microalgae, at least two of the following microalgae, at least three of the following microalgae, at least four of the following microalgae, at least five of the following microalgae, at least six of the following microalgae, at least seven of the following microalgae, at least eight of the following microalgae, at least nine of the following microalgae, at least ten of the following microalgae, or more. Microalgae in the consortium compositions of the present invention include, but are not limited to, *Scenedesmus dimorphus, Scenedesmus obliquus, Chlorella sorokiniana, Chlorella vulgaris, Cosmocladium perissum, Chlamydomonas sajao, Nannochloris* sp., *Micractinium* sp., *Scenedesmus quadricauda*, and *Chlamydomonas moewusii*. An aspect of the present invention comprises a microalgae composition comprising *Scenedesmus dimorphus, Scenedesmus obliquus, Chlorella sorokiniana, Chlorella vulgaris, Cosmocladium perissum, Chlamydomonas sajao, Nannochloris* sp., *Micractinium* sp., *Scenedesmus quadricauda*, and *Chlamydomonas moewusii* at a concentration of at least $1\times10^3$ cells per mL for each of the ten types of microalgae.

When combined to form a microalgae consortium composition, each of the microalgae listed above are combined in an amount of approximately $1\times10^3$ cells/mL, so that each is present in at least a concentration of $1\times10^3$ cells/mL. A microalgae consortium composition of the present invention comprises at least *Nannochloris* sp., *Scenedesmus quadricauda*, and *Chlorella vulgaris*, each of which is present in the microalgae consortium composition in at least a concentration of $1\times10^3$ cells/mL.

A microalgae consortium composition of the present invention may comprise microalgae other than those listed above. A microalgae consortium composition of the present invention may comprise microalgae with the following characteristics. 1) The microalgae will grow in the system described in U.S. patent application Ser. No. 13/115,975, which is herein incorporated in its entirety, and summarized herein, including the ability to be flocculated by *Paenibacillus polymyxa* strain, Strain 2, deposited under the Budapest Treaty as ATCC Accession No. PTA-12841. 2) The microalgae can be filtered by 200 mesh, which aids in elimination of filamentous algae and larger Protists. 3) The microalgae is a fresh-water algae and is able to live in the soil.

An aspect of the present invention comprises a microalgae consortium composition wherein the microalgae are found in a composition that used in methods of treatment disclosed herein such as a suspension of microalgae at a concentration of at least $30\times10^6$ cells per fluid oz. The microalgae cells may be found in such treatment solutions in concentrations in a range of from about $5\times10^6$ cells per fluid oz. to about $60\times10^6$ cells per fluid oz. For concentrated solutions, such as for shipping or storage, the microalgae may be found in higher concentrations. Though not wishing to be bound by any particular theory, it is thought that a majority of the cells in the suspension are stabilized in a stationary or non-growth phase.

An aspect of the present invention comprises a consortium composition comprising microalgae. As used herein, algae and microalgae may be used interchangeably and refer to single-celled organisms that are taxonomically known as microalgae. A microalgae composition of the present invention does not include filamentous algae.

Making Microalgae Compositions Described Herein.

Methods of the present invention comprise making microalgae compositions described herein. Microalgae compositions of the present invention comprise microalgae that are grown in fresh water conditions.

Figure 5:
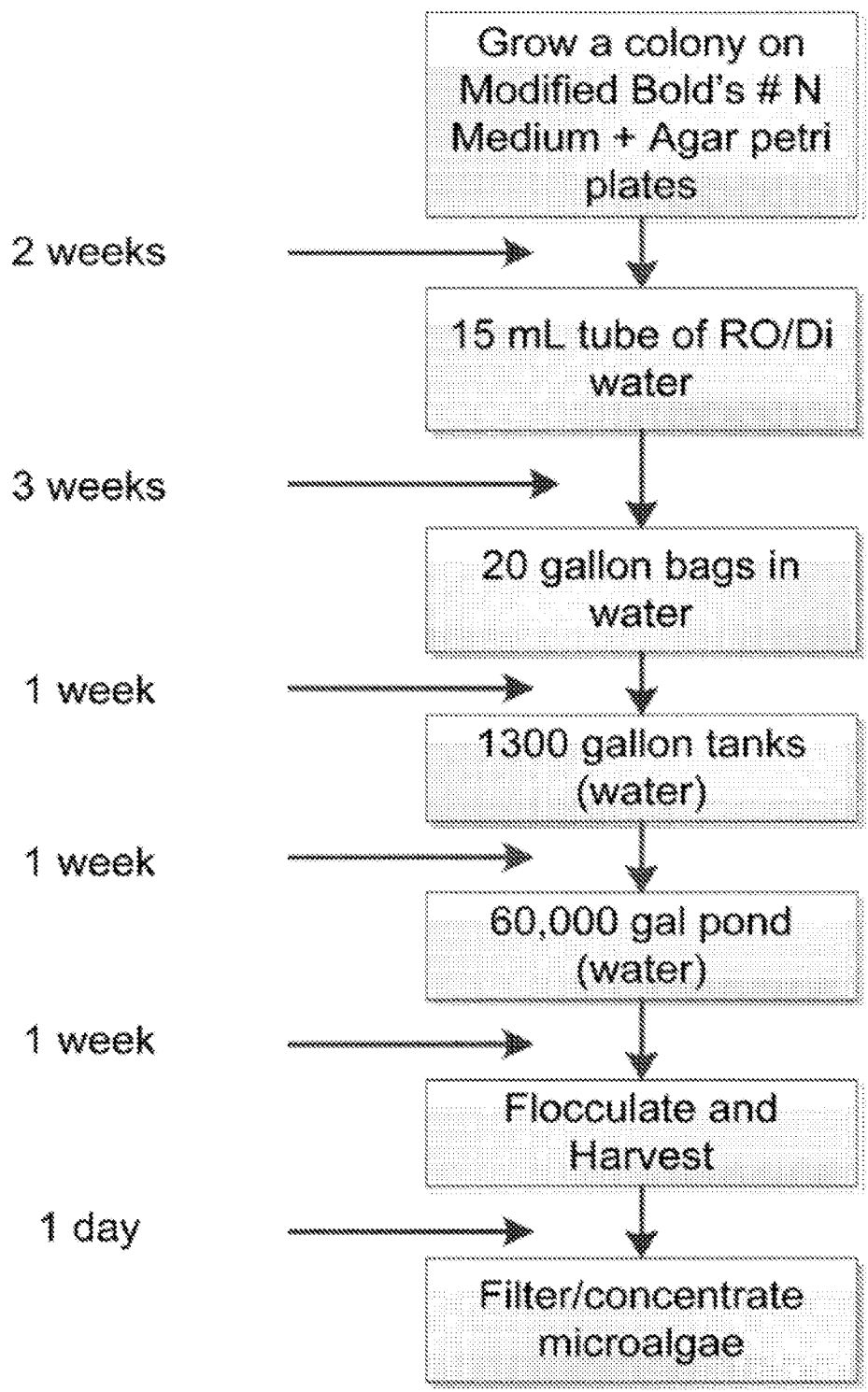
FIG. 5 shows a flowchart for growing an exemplary microalgae consortium composition of the present invention.

Microalgae may be grown by any method known for growing large amounts of microalgae. A method for growing microalgae is shown in FIG. 5 and summarized herein. A method for growing microalgae is disclosed in U.S. patent application Ser. No. 13/115,975, herein incorporated in its entirety. The present invention comprises methods and compositions for aggregating algae growing in containers, for example, large containers such as industrial ponds, so that the algae is harvested from one container and may be placed in a more concentrated amount in a second container, where the cells/mL is greatly increased over the original container.

Methods for obtaining concentrated biomass from an aqueous solution of microalgae, without causing the microalgae to be harmed significantly, such as ruptured, are desired. A method comprising flocculation with a bioflocculant, removal of the microalgae from a container, such as an industrial containment system or a pond, and containment of the microalgae in a higher concentration in a smaller container is taught in U.S. patent application Ser. No. 13/115,975. Flocculation of a microalgae suspension in a reservoir or container, for example, an industrial-sized pond, by application or provision of a bioflocculant is used to obtain quantities of microalgae. Flocculation of the algae may occur over several days, such as from one to six days, for one day, for two days, for three days, for four days, for five days, or for six days, referred to herein as a flocculation period. It is desired that during the flocculation period, the algae are not exposed to extreme hypoxic situations or complete loss of exposure to light, as the algae settle to the lower regions of the container. One skilled in the art can determine the time for adequate flocculation by monitoring the condition of the algae during the flocculation period to maintain good care of the algae. The bioflocculant may be one or more strains of bacteria that may or may not be specific for one or more species of algae. The flocculated suspension of algal cells may be removed via pumping or other removal methods to a smaller container, where the number of algal cells per milliliter of fluid is much greater than was the concentration of algal cells in the original container or reservoir. A particular flocculent that may be used is *Paenibacillus polymyxa* strain, Strain 2, deposited under the Budapest Treaty as ATCC Accession No. PTA-12841.

Microalgae are first grown on small cultures from frozen or stored stock sources for each type of microalgae. After 2 weeks of growth, the algae are expanded to 15 ml tubes in water with nutrients. After about three weeks, the tube contents are transferred to 20 gallon bags of water and nutrients. After about 1 week, the contents of the 20 gallon bags are transferred to a 1300 gallon tank with water and nutrients. After about a week of growth, the contents of the 1300 gallon tank are transferred to a 60,000 gallon pond with water and nutrients. It is at the 60,000 gallon pond that multiple types of microalgae, expanded as described, are comingled. After about 1 week of growth in the large pond, the microalgae are flocculated and harvested from the ponds with pumps. The isolated microalgae are filtered and concentrated, screened for pathogens and the cell density is determined. The algae may be then stored at 55 degrees.

After harvesting the microalgae and concentrating them, the microalgae are not fed and generally enter into a dormant state. The microalgae are filtered and stabilized with xanthum gum or other agents that may stabilize the algae and control the algae osmostic potential. A final microalgae consortium composition has a high concentration of microalgae suspended in a liquid, such as water, and is not found as a paste. The shelf-life of the concentrated microalgae consortium composition may be from 30 days, from 60 days, from 90 days, from more than a year. It is preferred to maintain the concentrated microalgae consortium composition at room temperature or below, and it can be frozen.

TABLE 1

Treatment and applications for plot 3. Plot size: 4 rows per variety. Planting population: 35,500.

| Crop/plot info | Treatment(s) | Description | Application | No. Applications |
|---|---|---|---|---|
| Approximate area: 0.5 acres Corn planting date May Harvest 5 months post planting Plots subject to high winds | Strip-Till: fertilizer applied | NPK: 20.5-35.8-0 | 10 gallons at 4 inches seedling height and 15 gallons at 10 inches height | 1, 1 month before planting |
| | Starter: applied with tractor | NPK: 30-40-0-45-0.053 Zn | 2 inches to the side and 2 inches below the seed at 18 gal per acre | 1, 4 days post planting |
| | Sprinkler irrigation | NPK: 28-0-0-5 | | 4, starting one month post planting, then every two weeks. |
| | Degree Xtra | Herbicide | 3 qt/acre | 1, 1 week before planting |
| | Round-Up | Herbicide | 32 oz/acre | 1, 1 week before planting |
| | Class Act | Herbicide adjuvant | 0.54 qt/acre | 1, 1 week before planting |
| | Round-Up | Herbicide | 32 oz/acre | 1, 6 weeks post planting |
| | AMS 17 | Herbicide adjuvant | 100 gal. | 1, 1 week before planting |
| | GOgreen ™ | 4 weeks post-emergence | 10 oz/acre | 1, 4 weeks post planting |
| | GOgreen ™ | 8 weeks Post-emergence | 10 oz/acre | 1, 8 weeks post planting |
| | No GOgreen ™ | To Plot 5 | Control | N/A |

NPK: Nitrogen, Phosphorus, and Potassium content.

TABLE 2

Treatment and applications for plots 1-4 and control during 2011. Plot size: 4 rows per variety. All plots were divided into high (8.3) and low pH (6.8). Planting population: 34,000.

| Crop/plot info | Treatment(s) | Description | Application | Date(s) of Application |
|---|---|---|---|---|
| Approximate area: 0.5 acres Corn planting date May Harvest date November Plots subject to high winds | Strip-Till: fertilizer applied while strip tilling | NPK to all plots 9-15-0 | 8 gallons at 4 inches seedling height and 13 gallons at 10 inches height | 1 month pre-planting |
| | Starter: applied with | NPK to all plots 15-20-0-2. Os- | 2 inches to the side and 2 inches below | Day of |
| | Sprinkler irrigation | NPK to all plots 32-0-0 | 10 gal./acre 4 gal./acre | 6 weeks post planting 8 weeks |
| | Degree Xtra | Herbicide to all plots | 2.9 qt/acre | 1 week pre-planting |
| | Round-Up | Herbicide to all plots | 32 oz/acre | 1 week pre-planting |
| | Synurgize | Glyphosate adjuvant | 1 qt/100 gal of H20 | 1 week pre-planting |
| | Non-ionic surfactant | Herbicide to all plots | 32 oz/100 gal./acre | 5 weeks post |
| | Round-Up Weathermax | Herbicide to all plots | 32 oz/acre | 5 weeks post planting |
| | AMS 17 | Herbicide to all plots | 17 lbs/100 gal./acre | 5 weeks post planting |
| | GOgreen ™ | To Plot 1 only | 10 oz/acre | 5 weeks post planting and |
| | GOgreen ™ | To Plot 2 only | 8 oz/acre (half label dosage) | 6 weeks post planting and 7 weeks post planting |

TABLE 2-continued

Treatment and applications for plots 1-4 and control during 2011.
Plot size: 4 rows per variety. All plots were divided into high
(8.3) and low pH (6.8). Planting population: 34,000.

| Crop/plot info | Treatment(s) | Description | Application | Date(s) of Application |
|---|---|---|---|---|
| | GOgreen ™ | To Plot 3 only | 10 oz/acre | 6 weeks post planting and 7 weeks post planting and 8 weeks post planting |
| | GOgreen ™ | To Plot 4 only | 20 oz/acre | 6 weeks post planting and 7 weeks |
| | No GOgreen ™ treatment | To Plot 5 | Control | N/A |

(N/A = not applicable;
*second treatment in consecutive years).

TABLE 3

Soil analysis for all plots pre-algae treatment. All units
in parts per million (ppm) unless otherwise noted.

| Sample ID | pH | OM(%) | CEC (meq/100 g) |
|---|---|---|---|
| Control L | 6.90 | 0.90 | 10.60 |
| Plot 2 L-post | 7.70 | 0.70 | 9.10 |
| Plot 1 L-post | 7.30 | 0.80 | 11.20 |
| Plot 3* L-post | 7.70 | 0.70 | 10.60 |
| Plot 4 L-post | 7.60 | 0.70 | 11.80 |
| Control L post-2 M | 7.00 | 0.90 | 8.20 |
| Plot 2 L post-2 M | 7.00 | 1.00 | 8.10 |
| Plot 1 L post-2 M | 7.20 | 1.10 | 8.00 |
| Plot 3* L post-2 M | 6.90 | 1.10 | 8.60 |
| Plot 4 L post-2 M | 6.90 | 1.00 | 8.60 |
| Control H-post | 8.20 | 1.00 | 17.60 |
| Plot 2 H-post | 8.30 | 1.00 | 18.30 |
| Plot 1 H-post | 8.20 | 1.10 | 16.50 |
| Plot 3* H-post | 8.30 | 1.30 | 18.40 |
| Plot 4 H-post | 8.10 | 1.10 | 16.30 |
| Control H post-2 M | 7.90 | 0.70 | 9.50 |
| Plot 2 H post-2 M | 7.80 | 0.80 | 11.50 |
| Plot 1 H post-2 M | 7.70 | 0.70 | 7.50 |
| Plot 3* H post-2 M | 8.40 | 0.90 | 11.00 |
| Plot 4 H post-2 M | 8.30 | 0.80 | 14.30 |

*indicates pre- GOgreen ™treatment the previous year.
Abbreviations: OM(%) = Percent Organic Matter, CEC = Cation Exchange Capacity. L = pH < 8.0, H = pH > 8.0 post = after GOgreen ™ treatment. Post-2 M = 2 months after harvest.

REFERENCES

1. Alexander, M., 1977. Introduction to Soil Microbiology. Wiley, N.Y.
2. Beakes, G., Canter, H. M. and G. H. M Jaworski. 1988. Zoospores. ultrastructure of *Zygorhizidium affluens* Canter and *Z. planktonicum* Canter, two chytrids parasitizing the diatom *Asterionella formosa* Hassall. Can. J. Bot. 66: 1054-1067.
3. Berard A. and C. Benninghoff. 2001. Pollution-induced community tolerance (PICT) and seasonal variations in the sensitivity of phytoplankton to atrazine in nanocosms, Chemosphere 45: 427-437.
4. Berard A., Leboulanger C. and T. Pelte. 1999. Tolerance of *Oscillatoria limnetica* Lemmermann to atrazine in natural phytoplankton populations and in pure culture: Influence of Season and Temperature, Arch. Environ. Con. Tox. 37:472-479.
5. Bold, H. C. 1949. The morphology of *Chlamydomonas chlamydogama* sp. nov. Bull. Torrey Bot. Club. 76: 101-8.
6. Bot, A. and J. Benites. 2005. The importance of soil organic matter, key to drought-resistant soil and sustained food production. FAO Soils Bulletin 80. Rome (Italy): FAO.
7. Brock, T. D. 1973. Primary colonization of Surtscy, with special reference to the blue-green algae. Oikos 24:239-243.
8. Charles, D., Aker, F. and N. A. Roberts. 1996. Diatom periphyton in Montana lakes and wetlands: ecology and potential as bioassessment indicators. Patrick Center of Environmental Research, Environmental Research Division. The Academy of Natural Sciences, Philadelphia, Pa., USA.
9. Gaydon, D. S., Probert, M. E., Buresh, R. J., Meinke, H. and J. Timsina. 2012. Modelling the role of algae in rice crop nutrition and soil organic carbon maintenance. European Journal of Agronomy, 39: 35-43.
10. Doherty, S. M., Cohen, M. Lane, C. Line, L. and J. Surdick. 2000. Biological criteria for inland freshwater wetlands in Florida: a review of technical and scientific literature (1990-1999). Report to the United States Environmental Protection Agency, Center for Wetlands, University of Florida, Gainesville, Fla., USA.
11. Doran, J. W. and T. B. Parkin. 1994. Defining and assessing soil quality. p. 3-21. In: J. W. Doran, D. C. Coleman, D. F. Bezdicek, and B. A. Stewart (eds.), Defining Soil Quality for a Sustainable Environment. SSSA Spec. Pub. No. 35, Soil Sci. Soc. Am., Am. Soc. Argon., Madison, Wis.
12. Elliott, E. T., Paustian, K. and S. D. Frey. 1996. Modeling the measurable or measuring the modelable: a hierarchical approach to isolating meaningful soil organic matter fractionations. In: Powlson, D. S., Smith, P., Smith, J. U. (Eds.), Evaluation of Soil Organic Matter Models. Springer-Verlag, pp. 161-179, NATO ASI Series.
13. Fujita Y. and H. Nakahara. 1999. Effects of cultivation conditions on algal communities in paddy soils, Jap. J. Limnol. 60: 77-86.
14. Gerson U. 1974. The associations of algae with arthropods, Rev. Algol. 11: 18-41.
15. Abu, G. O., Ogbonda, K. H. and E. Aminigo. 2007. Optimization studies of biomass productionand protein biosynthesis in a *Spirulina* sp. isolated from an oil-polluted flamepit in the Niger Delta. Afr. J. Biotechnol. 6: 2550-4.

16. Goyal, S. K. 1997. Algae and the soil environment. Phykos 36: 1-13.
17. Hargrove, W. W. and R. J. Luxmore. 1988. A New High-Resolution National Map of Vegetation Ecoregions Produced Empirically Using Multivariate Spatial Clustering. Available at http://gis.esri.com/library/userconf/proc98/proceed/TO350/PAP333/P333.HTM.
18. Havlin, J. L., J. D. Beaton, S. L. Tisdale, and W. L. Nelson. 1999. Soil Fertility and Fertilizers. 6th Edition. Prentice Hall. Upper Saddle River, N.J. 499 p.
19. Hoffmann L. 1989. Algae of terrestrial habitats, Bot. Rev. 55:77-105.
20. Johansen, J. R. 1993. Cryptogamic crusts of semiarid and arid lands of North America. J. Phycol. 29: 140-147.
21. Pandey, J. P. and A. Tiwari. 2010. Optimization of biomass production of *Spirulina maxima*. J. Algal Biomass Utilization. 1: 20-32.
22. Kennedy, A. C., and R. I. Papendick. 1995. Microbial characteristics of soil quality. Journal of Soil and Water Conservation 50:243-248.
23. Kostikov I. J, Romanenko, P. O., Demchenko, E. M., Darienko, T. M., Mikhayljuk, T. I., Rybchnnskiy, O. V. and A. M. Solonenko. 2001. Soil algae of Ukraine (Vodorosti gruntiv Ukrajiny).—300 pp., Phytosotsiologichniy center, Kiev.
24. Kuzyakhmetov, G. G. 1998. Algological evaluation of the toxicity of copper compounds in grey forest soil and leached chernozem. Eurasian Soil Sci. 31: 877-882.
25. Lukesova, A. 2001. Soil algae in brown coal and lignite post-mining areas in Central Europe (Czech Republic and Germany). Restoration Ecol. 9: 341-350.
26. Lukesova, A. and L. Hoffmann. 1996. Soil algae from acid rain impacted forest areas of the Krusnehory Mountains. Algal communities. Vegetation 125:123-136.
27. Lukesova, A. and L. Hoffmann. 1995. Soil algae from acid rain impacted forest areas of the Krusnehory Mountains. Effect of pH on growth. Algological Stud. 78: 39-51.
28. Lukesova, A. A. 1993. Soil algae in four secondary successional stages on abandoned fields. Algological Stud. 71: 81102.
29. Malakar, E. and M. C. Kalita 2012. A perspective towards development and commercialization of potential bga biofertilizers of Assam, North East India and carrier materials for BGA mass production and Inoculum development. Annals of Biological Research. 3: 814-828.
30. McCann, A. E. and D. R. Cullimore. 1979. Influence of pesticides on the soil algal flora. Residue Rev. 72: 1-32.
31. Megharaj, M., Singleton, I., Kookana, R. and R. Naidu. 1999. Persistence and effects of fenamiphos on native algal populations and enzymatic activities in soil. Soil Biol. Biochem. 31: 1549-1553.
32. Metting, B. 1981. The systematics and ecology of soil algae. Bot. Rev. 47: 195-312.
33. Metting, B. and W. Rayburn. 1979. Algal communities and soil microenvironments in an Eastern Washington silt loam. Soil Sci. 127: 74-78.
34. Mostafa, F. I. Y. and C. S. Helling. 2002. Impact of four pesticides on growth and metabolic activities of two photosynthetic algae. J. Environ. Sci. Health B 37:417-444.
35. Neustupa, J. 2001. Soil algae from marlstone-substratum based biotopes in the Nature park Dzban (Central Bohemia, Czech Republic) with special attention to the natural treeless localities. Algological Stud. 101:109-120.
36. Pan, Y. and R. J. Stevenson. 1996. Gradient analysis of diatom assemblages in western Kentucky wetlands. Journal of Phycology 32: 222-232.
37. Pankhurst, C., Doube, B. M. and V. V. S. R. Gupta. 1997. Biological Indicators of Soil Health, CAB International, London, pp.
38. Paoletti, M. G. 1999. Some unorthodox thoughts: what Western agriculture should learn from Chinese agriculture. Critical review in Plant Sciences 18: 475-487.
39. Paoletti, M. G. 1988. Soil invertebrates in cultivated and uncultivated soils in North-East Italy. Redia 71: 501-563.
40. Paul, E. A. and F. E. Clark. 1989. Soil Microbiology and Biochemistry. Academic Press, Inc. San Diego. 275 p.
41. Pipe, A. E. 1992. Pesticide effects on soil algae and cyanobacteria, Rev. Environ. Contam. T. 127: 95-171.
42. Pipe, A. E. and D. R. Cullimore. 1980. An implanted slide technique for examining the effects of the herbicide Diuron on soil algae. Bulletin of Environmental Contamination and Toxicology 24: 306-312.
43. Roper M. M. and K. M. Ophel-Keller. 1997. Soil microflora as bioindicators of soil health, in: Pankhurst C. E., Doube B. M., Gupta V. V. S. R. (Eds.), Biological indicators of soil health, pp. 157-177.
44. Roper M M and V. V. S. R. Gupta. 1995. Management practices and soil biota. Australian Journal of Soil Research. 33: 321-339.
45. Ruble, R. W. and J. S. Davis. 1988. Soil algae from fallow potato fields in south Florida (USA) marl. Nova Hedwigia 47: 403-414.
46. Sims, G. K. 1990. Biological degradation of soil. Advances in Soil Science. 11:289-329.
47. Sparling, G. P. 1997. Soil microbial biomass, activity and nutrient cycling as indicators of soil health. Biological Indicators of Soil Health, ed. C. E. Pankurst, B. N. Doube, & V. S. R. Gupta, CAB: Wallingford, 4: 97-119.
48. Stanier R. Y., Kunisawa, R., Mandel, M. and G. Cohen-Bazire. 1971. Purification and properties of unicellular bluegreen algae (Order: Chroococcales). Bacteriological Reviews. 35: 171-305.
49. Starks, T. L., Shubert, L. E. and F. R. Trainor. 1981. Ecology of soil algae: a review. Phycologia 20: 65-80.
50. Stevenson, R. J. 2001. Using algae to assess wetlands with multivariate statistics, multimetric indices, and an ecological risk assessment framework. Pages 113-140 in D. P. Batzer, R. B. Rader, and S. A. Wissinger, editors. Bioassessment and management of North American freshwater wetlands. John Wiley and Sons, New York, N.Y., USA.
51. Sukala, B. L. and J. S. Davis. 1994. Algae from non-fertilized soils and soils treated with fertilizers and lime of North Central Florida. Nova Hedwigia 59: 33-46.
52. Heger, T. J., Straub, F. and E. A. D. Mitchell. 2012. Impact of farming practices on soil diatoms and testate amoebae: A pilot study in the DOK-trial at Therwil, Switzerland, European Journal of Soil Biology. 49: 31-36.
53. Thirup, L., Ekelund, F., Johnsen, K. and C. S. Jacobsen. 2000. Population dynamics of the fast-growing sub-populations of Pseudmonas and total bacteria, and their protozoan grazers, revealed by fenpropimorph treatment, Soil Biol. Biochem. 32: 1615-1623.
54. Tsujimura, S., Nakahara, H. and N. Ishida. 2000. Estimation of soil algal biomass in salinized irrigation land: a comparison of culture dilution and chlorophyll a extraction methods. J. Appl. Phycol. 12: 1-8.
55. van Dam, H., Mertens, A. and J. Sinkeldam. 1994. A coded checklist and ecological indicator values of freshwater diatoms from the Netherlands. Netherlands Journal of Aquatic Ecology 28: 117-133.
56. Warkentin, B. 1995. The changing concept of soil quality. J. Soil Water Conserv. 50: 226-228.
57. Whitton, B. A. 2000. Soils and rice-field, in: Whitton B. A., Potts M. (Eds.), The Ecology of Cyanobacteria, their diversity in time and space, pp. 233-255.
58. Yeates, G. W., Bongers, T., de Goede, R. G. M., Freckman, D. W. and S. S. Georgieva. 1993. Feeding habits in soil nematodes families and genera: an outline for soil ecologists. J. Nematol. 25: 315-331.
59. Zancan, S., Trevisan, R. and M. G. Paoletti. 2006. Soil algae composition under different agro-ecosystems in North-Eastern Italy. Agriculture, Ecosystems and Environment 112: 1-12.
60. Zenova, G. M., Shtina, E. A., Dedysh, S. N., Glagoleva, O. B., Likhacheva, A. A. and T. A. Gracheva. 1995. Ecological relations of algae in biocenoses. Mikrobiologiya 64: 121-133.
61. Zurek, L. 1981. The Influence of the Herbicides Lenacil and Pyrazon on the Soil Algae. Ekologia polska-Polish. Pol. J. Ecol. 29: 327-342.

EXAMPLES

Example 1

Materials and Methods

Soil Treatments

Experimental plots of approximately 0.5 acres each were planted with corn in four rows. Plots were designated by numbers based on the application rate of a microalgae consortium composition of the present invention comprising *Chlorella sorokiniana* $2.4 \times 10^6$, *Chlorella vulgaris* $1.7 \times 10^6$, *Chlamydomonas moewusii* $0.6 \times 10^6$, *Nannochloris* $1.1 \times 10^6$, *Scenedesmus obliquus* $1.5 \times 10^6$, *Scenedesmus dimorphus* $2.0 \times 10^5$, *Scenedesmus quadricauda* $1.0 \times 10^5$, *Micractinium* $2 \times 10^4$, *Chlamydomonas sajao* $2 \times 10^4$, *Cosmocladium perissum* $3 \times 10^3$, referred to herein as GOgreen or GOgreen™. Therefore, plot 1 (recommended 10 oz/acre), plot 2 (8 oz/acre), plot 3 (10 oz/acre) and plot 4 (20 oz/acre). A control plot (plot 5) was also included. Corn (34,000 plants per acre) was planted in May 2011 and harvested in November 2011 allowing each plot to be studied for 6 months. In order to study the effects of consecutive planting and harvesting on algae populations in the soil, one plot (plot 3) was planted in May 2010 and harvested in October 2010. Treatment for this plot is shown in Table 1.

Soil Analysis

Soil samples from each of the experimental and control plots were taken at a depth of 6 inches immediately after herbicide application. These samples were labeled pre-treatment. Analysis included organic matter content, phosphorus as P1 (weak, Bray), potassium (K), Magnesium (Mg), Calcium (Ca), Sodium (Na), pH, cation exchange capacity (CEC), percent base saturation (% K, % Mg, % Ca, % H, % Na), nitrate-N (FIA), Sulfur (S), Zinc (Zn), Manganese (Mn), Iron (Fe), Copper (Cu), Boron (B) and soluble salts.

Each plot received all treatments listed in Tables 1 and 2 except for the controls. Controls were not treated with GOgreen. Prior to harvest, soil samples were taken from each of the plots (and control). These samples were labeled post-GOgreen™. Samples were also taken from each of the plots and controls 2 months after harvesting. These samples were labeled post-GOgreen™. 2 months. Each plot crossed a region of high soil pH (8.3) and neutral soil pH (6.8) and soil samples were taken individually from these regions. Treatments are described on Table 2. Plot 3 was again planted in May 2011 and harvested in November 2011 allowing for a year of consecutive corn harvesting and data recording on this plot.

Description of these treatments was relevant to our study because herbicides have been documented to have a detrimental effect on soil algae populations (Kuzyakhmetov, 1998; Zancan et al., 2006). GOgreen™ was delivered at the recommended application rate through center pivot irrigation before the V7 stage of corn plant growth. Soil samples were taken at V5 stage of plant growth as well as 4, 6, 7, and 8 weeks after emergence. A final sample was taken at harvest (black layer).

Algal Species Identification

Media and solutions were prepared using chemicals from Sigma-Aldrich (St. Louis, Mo.) unless otherwise noted. HEPES buffer (50 mM, pH 7.8) was used to prepare Vitamin B12, Biotin and Thiamine solutions. In order to culture algae for identification purposes, 1 gram of soil from each plot including high and low pH regions as separate samples was added to 10 mL of selective media and plated using Agar plates.

3N Modified Bold's Basal Media (Bold 1949) was used for enrichment of green, red, and brown algae. Soil water was prepared using an adaptation of E. G. Pringsheim's biphasic soil-water medium (Pringsheim, 1946). Diatom Medium (DM) was used to culture and identify diatoms (Beakes et al., 1988), Proteose medium (PM) was used for yellow-green algae. PM was made by adding proteose peptone to Bristol Medium at a final concentration of 1 g/L. Bristol medium was prepared according to Bold (1949). To culture cyanobacteria, BG-11 was used as previously described (Stanier et al., 1971). Cultures were grown at 16:8 under full spectrum grow lights for 4-6 weeks at 22° C. Algae layers (1 mL) were collected using a Pasteur pipette and plates of selective medium were inoculated. Colonies were counted and identified through light microscopy 6 days post-inoculation.

Results

Figure 1B:
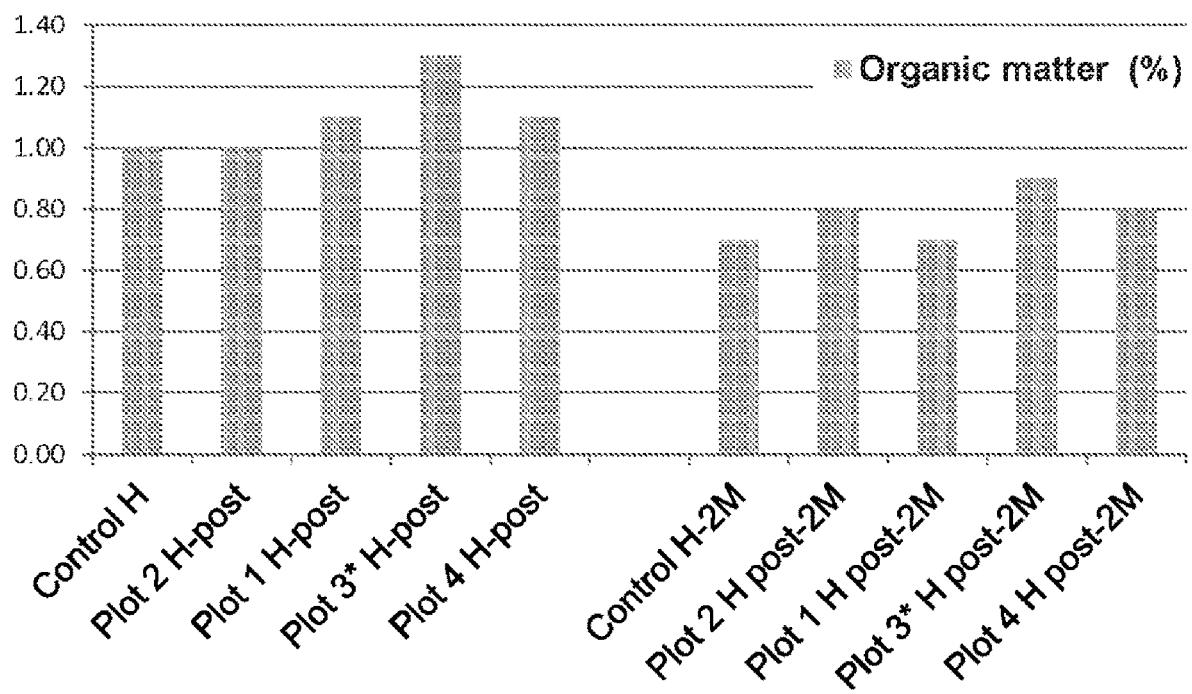

Results from soil analysis pre-treatment and after GOgreen™. treatment at harvest and 2 months post-harvest are shown in Table 1. Plot 2 values are shown prior to Plot 1 values as the dose applied in plot 2 was 8 oz./acre vs. 10 oz./acre applied in plot 1. This order facilitated comparison between a one-time application of GOgreen™ (plot 1) vs consecutive GOgreen™ application (plot 3). Percentages for OM were very low for all plots including control. This is typically observed in soils in the South West (Hargrove and Luxmore, 1988). Differences in OM and CEC pre and post-GOgreen™ treatment for each individual plot are shown in FIGS. 1A and 1B respectively.

Differences in Percent Organic Matter

Our results indicated that GOgreen™ had a significant effect in the OM content of soil at both pH values tested. Although lower OM values were observed prior to harvest in soil with pH<8.0 when compared with the controls (FIG. 1A (left)), an increase in OM was observed two months after harvest (FIG. 1A (right)). In soil with pH>8.0, GOgreen™ OM content values were higher prior to harvest when compared to those obtained at pH<8.0. In the first group, treatment with GOgreen™ at the recommended dose appeared to have a positive effect on CEC. Although GOgreen™ initially increased the OM content of the soil prior to harvest (FIG. 1B (left)) this effect was not sustained 2 months after harvest (FIG. 1B (right)) in this particular soil and/or crop type. It is worth noting that although the control at pH<8.0 did not show any changes in OM over time, the control at pH>8.0 showed a significant decrease in OM indicating that other factors independent of GOgreen™. application might have played a role in OM content measurements at high pH values.

Differences in Cation Exchange Capacity

Figure 2A:
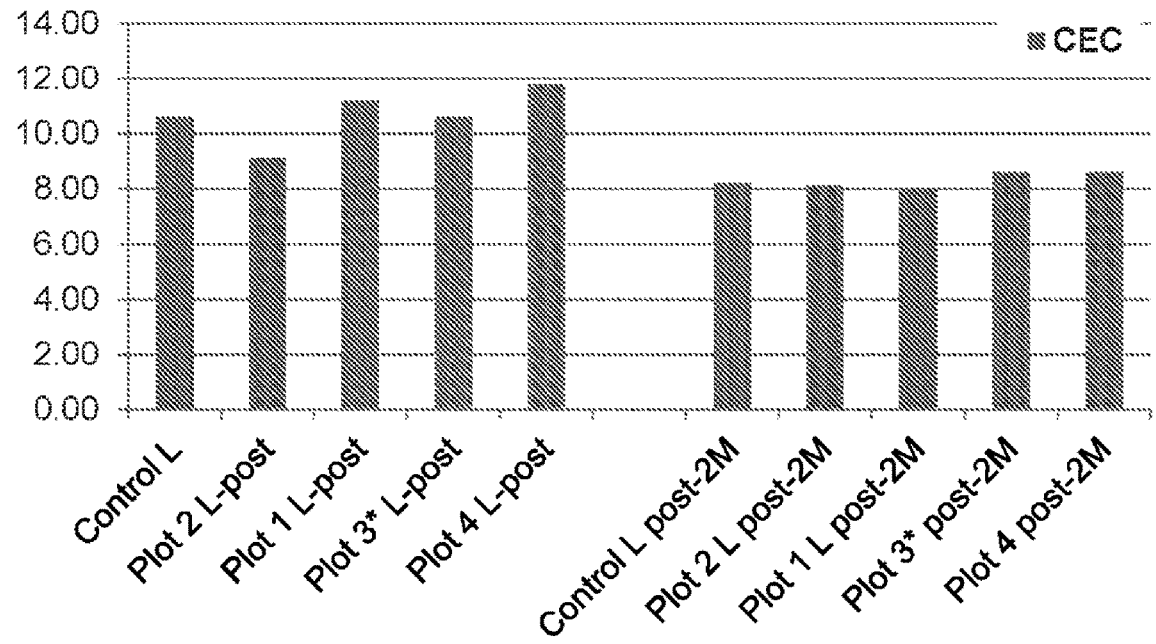
FIGS. 2A and 2B show differences in cation exchange capacity (CEM) before and after treatment with a microalgae consortium composition of the present invention.
Figure 2B:
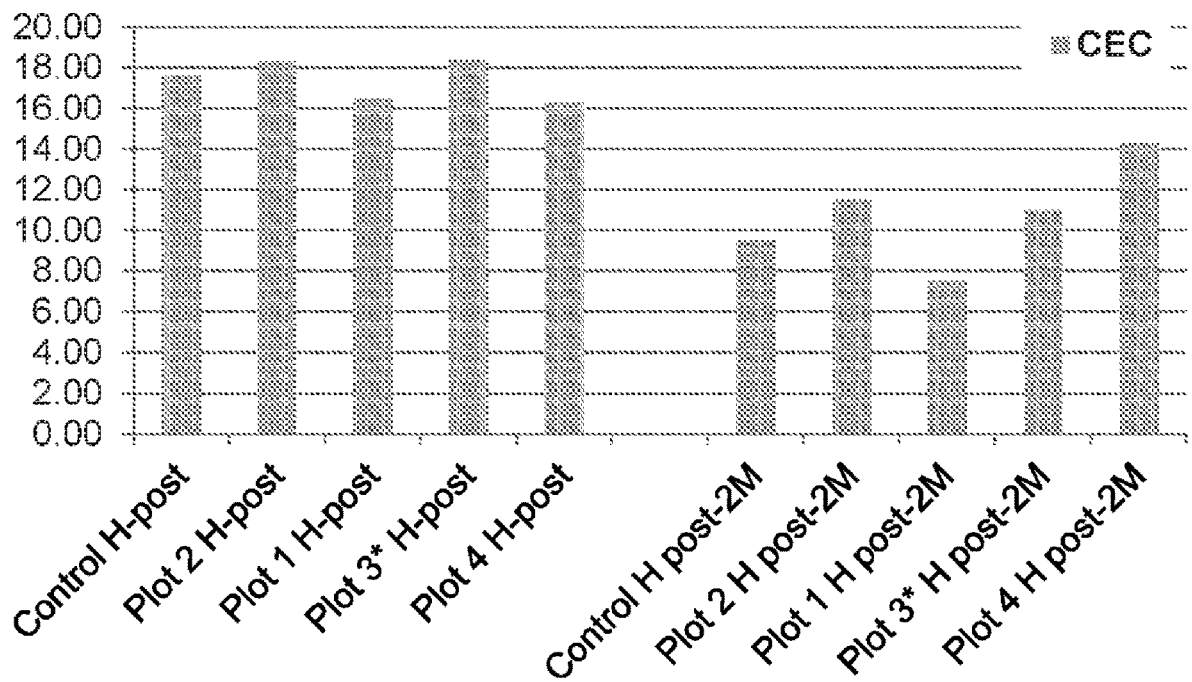

In terms of CEC, significant differences were observed in CEC two months after harvest when compared to samples collected prior to harvest (FIGS. 2A and 2B). It was observed that prior to harvest GOgreen™ treatment at the recommended 10 oz./acre increased the CEC of the soil in the treated plots at pH<8.0. The highest CEC obtained prior to harvest was observed at 20 oz./acre in the soil samples with pH<8.0. Two months after harvest, the CEC values declined for all plots in this group including the control and the values were uniform. The average CEC for all plots at harvest was 10.6 for the control at this pH value and the average for all plots was 10.68 indicating an increase of 0.08 units. There were no increases observed in CEC in the plots treated with GOgreen™ at pH>8.0 prior to harvest. Although the CEC values for the plots in the pH>8.0 group were significantly higher (by about 7 mel/100 g) when compared to the plots in the pH<8.0 group, two months after harvest, CEC values were also lower than those observed prior to harvest consistent with the CEC values observed for the pH<8.0 group.

Algal Species Diversity

Figure 3:
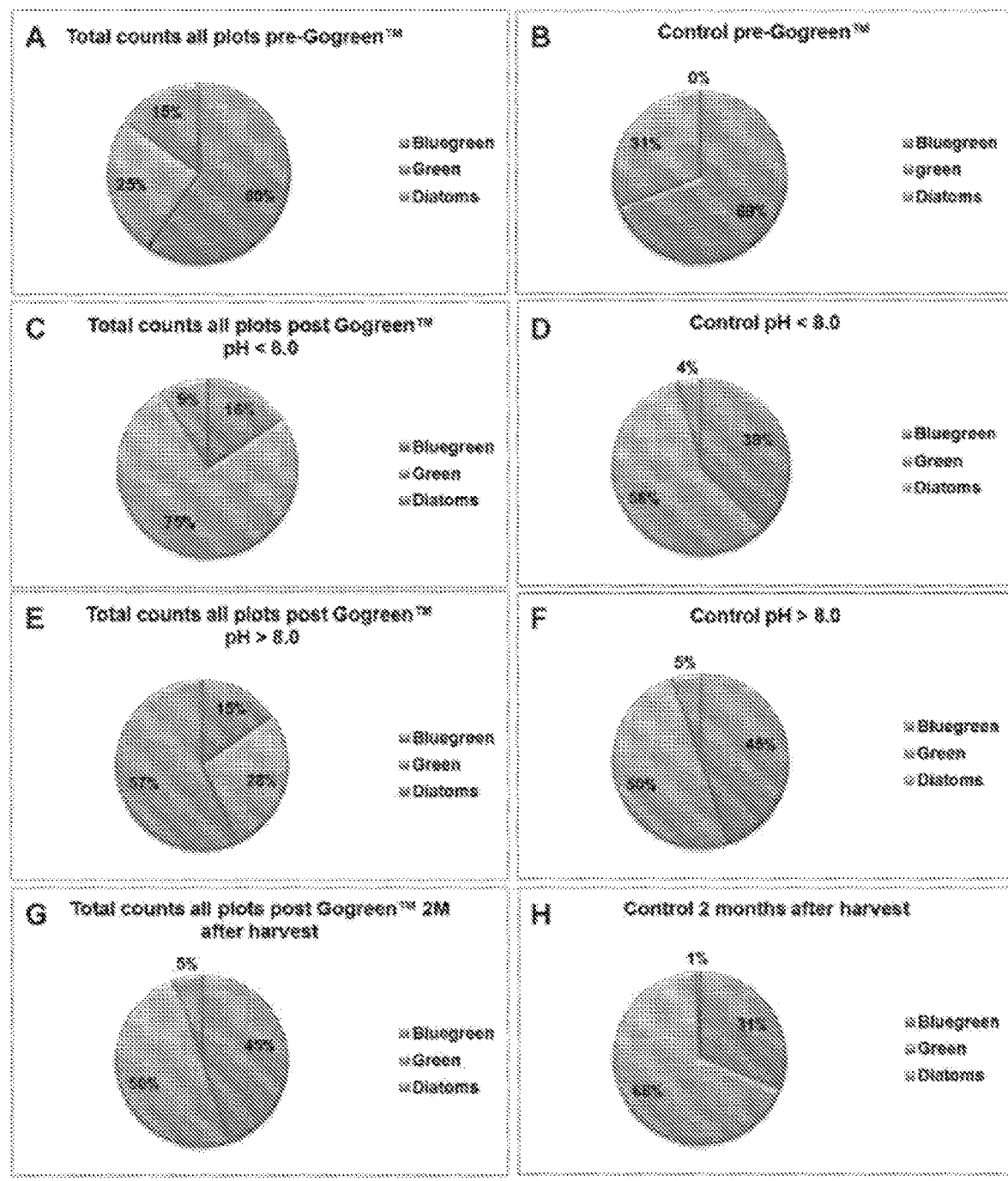
FIG. 3A-H show algal species diversity before and after treatment with a microalgae consortium composition of the present invention. Effects of pH in total counts of groups of species.

The effect of GOgreen™ was studied in plots before and after application. Total algae counts were grouped as percentages of blue-green and green algae as well as diatoms. Results are shown in FIG. 3.

The results indicate that prior to GOgreen™ treatment, the total microalgae population in the soil of the test plots was composed of 60% blue-green algae, 25% green algae and 15% diatoms (FIG. 3A). The ratio of green to blue-algae was 0.42. In the control plot, the ratio of green to blue-green algae pre-treatment was approximately 0.45 (FIG. 3B) indicating uniformity in the distribution of microalgae by plots before treatment.

In soils with pH<8.0, green algae were more abundant, which also correlated with the control at this pH (FIGS. 3C and 3D). The amount of diatoms was higher in the treated plots than the controls. In soils with pH>8.0, green algae counts were lower than those of blue algae (FIGS. 3E and 3F). However, the number of diatoms was higher in the treated plots when compared to the controls.

The results obtained two months after harvest indicate the percentages of blue-green algae and green algae were similar after GOgreen™ treatment (FIG. 3G). In contrast, the controls plots showed a 50% reduction in the blue-green algae counts when compared to the number of green algae (FIG. 3H). Although diatoms also appeared in the controls 2 months after harvest, their counts were significantly higher in the treated plots as shown in FIG. 3G.

The comparison between the pH<8.0 and the pH>8.0 controls indicates that there were small differences between their values (1.53 vs. 1.11 respectively). However, the difference between green and blue-green algae in the treated plots was significant (4.69 vs 1.87) indicating differences in microalgae diversity based on pH. In both cases, the ratio in terms of percentages was higher than the ratio of the controls indicating that treatment does have an impact on microalgae populations. Over time, all treated plots showed higher counts of green algae than blue-algae. When compared to untreated plots, those numbers showed a significant increase as the controls pre-treatment indicated higher numbers of blue-green algae in the soil. Furthermore, diatom concentrations increased in all treated plots. The counts were much higher in soil with pH>8.0.

Differences in Soil pH Before and after Treatment

Figure 4A:
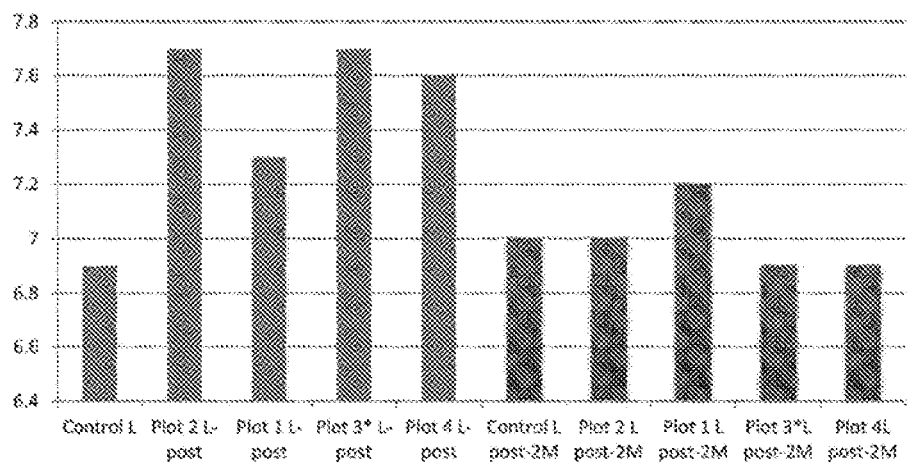
FIGS. 4A and 4B shows differences in soil pH before and after application with a microalgae consortium composition of the present invention.

The results of this study indicate significant differences between soil pH in the plots with pH<8.0 treated with GOgreen™ two months after harvest (FIG. 4A). Although the control plot did not show a significant change in pH (initial pH was 6.9 and pH after harvest was 7.0), the treated plots did show significant changes over time. A trend based on rates of application was not obvious.

It is clear from FIG. 4A that in plots with soil pH>7.0 at the end of harvest, the pH of the soil reached values closer to neutral two months later. In soils with pH>8.0 the trend was not as noticeable. However, pH decreased to values closer to 7.0 in plots 1 and 2, as well as the controls.

Figure 4B:
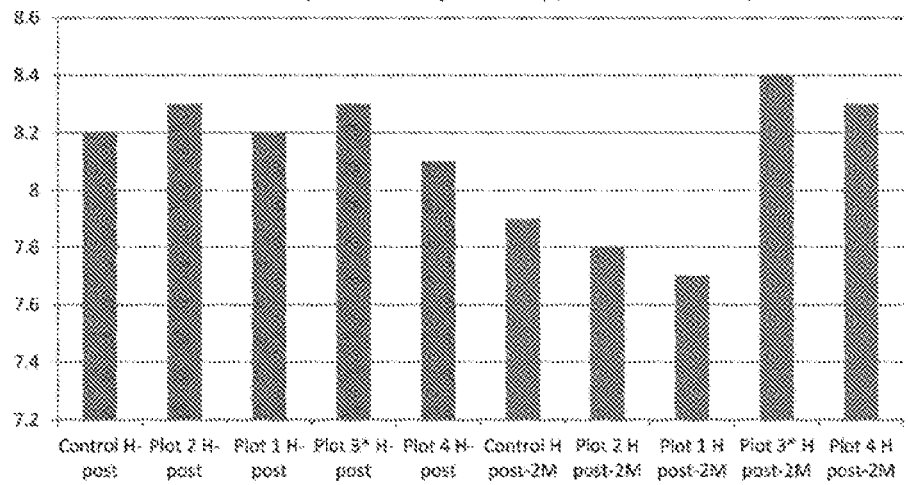

An observation worth noting is the difference in pH in plots 3 and plots 4 at pH>8.0 when compared to the other plots as seen in FIG. 4B. At this pH, treatment with GOgreen™ the previous year (plot 3) and with twice the recommended application rate (plot 4) resulted in a pH increase of 0.2 units two months after harvest when compared to the other plots. This result contradicts the observations in which pH decreased in the soil two months after harvest in plots 1 and 2.

Discussion

A classical approach was implemented to evaluate microalgae diversity in soil samples collected at a depth of 6 inches after herbicide and fertilizer treatment. Soil was treated with GOgreen™ in an effort to restore and improve microalgae diversity and soil properties. This method included isolation, culture and species identification based on morphological criteria. This method has been successfully used by other investigators (Kostikov et al., 2001).

The results presented herein demonstrate that treatment with GOgreen™ has significant and measurable effects on soil OM content, CEC, pH and microalgae species diversity suggesting positive effects of this formulation on soil conditions. Although studies in soil are affected by a variety of biotic and abiotic factors, the effects of GOgreen™ are evident. Abiotic factors considered in this study included light intensity, temperature and humidity. The most common biotic factors affecting soil quality were also considered. A separate manuscript is in preparation describing the effects of GOgreen™ on fungi, aerobic and anaerobic microbes. Control of external biotic and abiotic factors in the soil is extremely difficult and therefore the best approximation that could be done in a study of this nature is to compare soils that have been treated under the same conditions with simultaneous sampling.

Temperature changes in the environment during the time of the study were considered since it has been reported that blue-green algae are photo inhibited by high light intensities at low temperatures. Temperature can be considered as the most important limiting factor in outdoor cultivation during the winter (Malakar and Kalita, 2012). Blue-green algae growth is enhanced by increasing light density up to the point of light saturation, at which point photosynthetic activity reaches its maximum (Abu et al., 2007; Pandey and Tiwari, 2010). At high light densities, photosynthetic capacity decreases and blue-green algae growth is inhibited. As soil samples were taken from all plots during the cold months of November and February it is possible to hypothesize that the low counts of blue-green algae found in the treatment plots and the controls after GOgreen™ treatment are directly related to changes in ambient temperature and light intensity between soil sampling times. This could be a possible explanation for the differences encountered in the parameters measured between pre and post GOgreen™ applications. However, as all plots (treated and not treated) were exposed to the same environmental conditions, it is highly unlikely that the differences found in the treated plots versus the control plot were due to cold temperatures or intense light. The difference must be related to different soil characteristics as a result of treatment.

Despite abundant studies on soil algae (Metting, 1981; Starks and Shubert, 1981; Starks et al., 1981; Johansen, 1993; Lukesova, 1993; Sukala and Davis, 1994; Lukesova and Hoffmann, 1996; Tsujimura et al., 2000; Lukesova, 2001; Neustupa, 2001), it is still difficult to correlate species diversity and their influence on ecosystem functions. Therefore, this manuscript does not attempt to correlate species diversity with metabolic, ion or gas exchanges. Instead, the focus lies on algae species diversity after use of an organic formulation such as GOgreen™ and to correlate these findings with indicators of soil quality such as OM and CEC.

The primary objective of these studies was to determine the effects of the application of a commercial proprietary suspension of microalgae (GOgreen™) through a center pivot irrigation system in a crop of cultivated corn (*Zea mays*) on algae species diversity after herbicide application. The results of this study support the findings Zancan and Zuzyamkhmetov encountered in corn fields subjected to lengthy periods of intense fertilization. Their results indicate a reduction in species diversity and a suppression of blue-green algae development in fields treated with fertilizers and herbicides (Kuzyakhmetov, 1998; Zancan et al., 2006). The control shown in FIG. 3B, indicates low species diversity (diatoms are absent) encountered in the soil prior to GOgreen™ treatment but after fertilizer and herbicide treatment. The data shown confirms the profound effect of agricultural practices including herbicide and pesticide application on the structure of soil algal communities.

Herbicides have also previously been correlated to changes in microalgae populations in aquatic ecosystems (Berard et al., 1999; Berard and Benninghoff, 2001) and decreased density of algal assemblages in plots. Lenacil and Pyrazon for example, have been shown to diminish species diversity and decrease microalgae counts in soil (Zurek, 1981). Herbicides and pesticides influence the range of genera and the number of algal cells, blue-green in particular, present at any given time in vitro and in vivo (McCann and Cullimore, 1979; Metting and Rayburn, 1979; McCann and Cullimore, 1979; Megharaj et al., 1999; Mostafa and Helling, 2002).

One of the main groups considered a valuable tool to assess biological conditions in wetlands are the diatoms (Stevenson 2001; Doherty et al. 2000). The response of diatoms to changes in surrounding land and water column characteristics has been documented previously and many diatom taxa have been identified from a range of sites throughout the world. Diatoms appear to have a consistent tolerance of a wide range of environmental parameters, such as light, moisture, pH, salinity, oxygen and inorganic and organic nutrients (Van Dam et al., 1994). Responses to pH (Pan and Stevenson 1996) and heavy metal loading (Charles et al. 1996) have also been used to predict environmental pollution. The USEPA (2002) reported that diatoms are one of the most commonly used microorganisms in observations from aquatic ecosystems for assessing biological, physical, and chemical conditions. Through this study it can be concluded that GOgreen™ increased diatom numbers and species diversity in the treated plots compared to the controls indicating that GOgreen™ has a restorative effect on soil quality after herbicide treatment in heavily farmed soil. Additionally, these results indicate that the observations from aquatic ecosystems can be extrapolated to terrestrial environments.

In terms of specific differences in species diversity related to green and blue-green algae, a 17% increase was observed in the total counts of green microalgae in the GOgreen™ treated plots at pH<8.0 when compared to the control, while a 22% decrease was observed in blue-green algae in the same plots. Contrary to these results, a 22% decrease in green microalgae was observed in the GOgreen™ treated plots at pH>8.0 when compared to the controls, while a 30% decrease was observed in blue-green algae counts when compared to the control at this high pH value. These results indicate that the effects of GOgreen™ application are different and highly dependent on soil pH.

The pH of all plots tested varied between 6.9 to 8.4; therefore, many of the microalgal classes were represented. Blue-green algae are unable to survive in acidic conditions (Brock, 1973), but green algae are able to survive in soils with pH<7.0 (Lukesova and Hoffmann, 1995). Neutral conditions support the growth of algal communities representing all major taxonomic groups (Metting, 1981; Lukesova, 2001). The percentage of blue-green algae observed in the control plot at pH<8.0 was 38% (FIG. 3D) versus 45% in the control plot at pH>8.0 (FIG. 3F), which supports the findings by the above mentioned investigators. In contrast, the values for green algae in the two controls were similar (58% and 50%). These results indicate increased microalgal species diversity in the GOgreen™ treated plots versus the controls within the pH range tested.

An increase in diatom numbers and diversity was observed at all pH values when treatment plots were compared to controls not treated with GOgreen™. The results of treatment with GOgreen™ were different between soil with pH<8.0 and soil with pH>8.0. At all pH values, an increase in diatom concentration was observed in the GOgreen™ treated plots when compared to the controls, but this effect was higher in soils with pH>8.0, resulting in a 57% of total diversity composed of diatoms (FIG. 3E) versus 9% of diatoms at pH<8.0 (FIG. 3C). The main species found in the study were: *Fragilaria* sp., *Caposira*, *Tabellaria* sp., *Geminella*, *Navicula* sp., *Cyclotella* sp., *Tessillaria*, and *Pinnularia*.

The second objective of these studies was to determine the effect of GOgreen™ on OM and CEC. Both OM and CEC depend on soil pH. Optimum pH for corn ranges between 5.5-7.0 (Havlin et al., 1999). The results suggest that soils starting at pH<8.0 are most likely to fall within the optimal pH range for corn after GOgreen™ treatment.

Soil OM serves multiple functions including nutrient storage and soil aggregation. Soils with high CECs are able to bind more monovalent and divalent cations through available sites in clay and OM particles. A soil with a high CEC also has an increased buffering capacity indicating that this soil is able to resist fluctuations in pH.

Soils with a high clay content and/or OM will typically have higher CEC and buffering capacity than silty or sandy soils, as organic materials provide additional binding sites for cations. In this study, high OM correlated with high CEC values of the plots before GOgreen™ application. At harvest, CEC was higher in soil with pH>8.0, which is consistent with the presence of negative charges in the absence of acidic values that in turn have the ability to bind cations. Two months after harvest, values for CEC were lower at both pH ranges as it is expected after harvest due to soil depletion. These changes also correlated with pH values two months after harvest as the pH lowered for both types of soil. The most interesting observation was the fact that the CEC was around 8.0 at both pH values two months after harvest indicating a stabilization of CEC in the soil regardless of pH. Although this value is lower than those encountered at harvest, a low CEC value indicates that less cations such as K+, Ca2+, Mg2+, to name a few, will be less bound to soil particles and more available for nutrient uptake by the plant. Nitrogen will also be more available and less lime will be necessary to correct pH fluctuations. In soils with pH around 8.0 such as those found in the Western U.S., large amounts of naturally-occurring lime are typically responsible for the increased pH. This "free lime" buffers pH in the alkaline range making it very difficult to change soil pH. Calcium carbonate (CaCO3) is commonly found in these soils. For these particular soils, larger quantities of amendments are needed to lower the pH converting pH modification in alternatives that are not cost effective. Addition of organic matter is typically used to lower pH but not all sources of organic matter are effective or safe for human consumption. GOgreen™ lowers the pH in soils with a pH higher than 7.0 emerging as an economical alternative that is safe for humans and the environment.

In soil, the presence of living organisms has proven critical to OM formation. Soils with OM values around 1.0% are typically found in the desert. Soil OM—the product of on-site biological decomposition—affects the chemical and physical properties of the soil and its overall health. Its composition and breakdown rate affect: the soil structure and porosity; the water infiltration rate and moisture holding capacity of soils; the diversity and biological activity of soil organisms; and plant nutrient availability (Bot and Benites, 2005). Where the rate of OM addition is less than the rate of its decomposition the soil OM declines. Conversely, where the rate of addition is higher than the rate of decomposition, soil organic matter increases. The observations presented in this study regarding differences in OM at the pH values tested indicate that the rate of OM addition after GOgreen™ application is higher than the rate of decomposition in soils with pH<8.0. The opposite is true for soils with pH>8.0. However, further studies are needed to test this hypothesis. As changes in OM are lower than 1-2% per year of the total OM in the soil, the effects of GOgreen™ algae application will only become significant after several years. For this purpose, this study has been extended in order to monitor the plots described within this study during subsequent years of continuous harvest usage.

As land available for cultivation becomes scarce due to increasing populations, the need for improved soil quality is now recognized at a global scale (Elliott et al., 1996). Soil communities co-exist in constant interactions with each other (Gerson, 1974; Thirup et al., 2000; Yeates et al., 1993). These interactions are crucial to regulate soil activity and may be disturbed by soil pollution, herbicides, pesticides, fertilizers and management practices (Paoletti et al., 1988; Pankhurst, 1997).

Methods to determine soil quality are varied but scholars have identified microorganisms as potential bio indicators of soil quality (Pipe and Cullimore, 1980; Roper and Opel-Keller, 1997). It has been proposed that approaches to study ecological and eco-toxicological impacts of management and agricultural practices on soil quality should be monitored with the use of multimicrobial bio indicators. Soil microalgae depend on soil physical and chemical characteristics and therefore, these organisms have been used for decades as bio indicators to estimate Eco toxicological impact of agricultural management practices and herbicide application (Mc Cann and Cullimore, 1979; Pipe 1992; Fujita and Nakahara, 1999). Biodiversity is therefore an indicator of soil quality and a crucial component to evaluate the success of a particular remediation strategy. The use of biodiversity as an indicator is limited by the incomplete knowledge regarding microorganisms present in a particular ecosystem (Paoletti, 1999).

Microalgae and diatoms in particular respond to different ecological gradients and therefore are useful tools for bio monitoring studies in aquatic and terrestrial ecosystems. It has been demonstrated that diatom diversity tends to be higher in biodynamic systems than in conventional systems. Redundancy analysis (RDA) has suggested that diatom community structure differs significantly between organic and conventional systems (Heger et al., 2012).

Microalgae concentrate in the top few inches of the soil because they need moisture and light to perform photosynthesis. They are located in the first biological layer directly affected by environmental changes both natural and man-made. Consequently, microalgae composition varies in the soil over several weeks depending on treatment and their numbers are highly influenced by environmental and seasonal factors specific to each region (Hoffmann, 1989; Metting, 1981; Whitton, 2000). These results corroborate previous findings and highlight the importance of CEC, OM and pH variations in increased microalgae species diversity through GOgreen™ application.

Example 2

Table Grapes in Central Coast of California

The soil in which table grapes were treated with the composition of Example 1. The microalgae consortium composition was added to water and grown in an open tank, a photobioreactor. Treatment of the soil was continuous at >20,000 cells per mL at 7.5 gal/hour for the whole season of 6 months. The microalgae consortium composition was applied directly into a drip irrigation system, 24 hours a day, 7 days a week, for 6 months. In the soil, the nitrogen intake was increased 19.5% on average, and the phosphorus intake was increased 19.0% on average. See Tables 3 and 4 below.

TABLE 3

| Sample ID | Pre Treat N | Post Treat N |
|---|---|---|
| 1A | 65 ppm | 93 ppm |
| 1B | 59 ppm | 63 ppm |
| 2A | 60 ppm | 93 ppm |
| 2B | 73 ppm | 76 ppm |

TABLE 4

| Sample ID | Pre Treat P | Post Treat P |
|---|---|---|
| 1A | .21% | .26% |
| 1B | .21% | .26% |
| 2A | .20% | .24% |
| 2B | .20% | .25% |

Example 3

Sodium Levels in Plants and Soil

Corn was grown in Eastern Colorado and the soil was treated with a composition as described in Example 1, wherein the composition was diluted 1:100 in water and sprayed on the soil by the irrigation system. The objective of the study was to observe the reduction in sodium uptake by plants. The sodium level in the soil increases while the plant tissue sodium level decreases. Sodium in plant tissue (Stage of growth V7) is reduced by 33%. Plant tissue analysis was performed by Midwest Labs of Omaha, Nebr. See the results at Table 5.

TABLE 5

| Sample ID | % Sodium Pre-treated Soil | % Sodium Post-treated Soil | % Sodium Pre-treated Plant Tissue | % Sodium Post-treated Plant Tissue |
|---|---|---|---|---|
| Check plot | 21 | 26 | 0.002 | 0.009 |
| GOgreen ™ Treated plot | 21 | 34 | 0.002 | 0.006 |

Example 6

Measuring Cation Exchange Changes after Application of Microalgae Composition

On a test plot in Central Arizona, jalapeno peppers were grown with the composition of Example 1. The microalgae consortium composition was added to water and grown in an open tank, a photobioreactor. Treatment of the soil was continuous at >20,000 cells per mL at 7.5 gal/hour for the whole season of 4 months. The microalgae consortium composition was applied directly into a drip irrigation system, and was applied to the soil 24 hours a day, 7 days a week, for 6 months. The study was undertaken to study the changes in soil capacity to exchange ions. CEC, Cation Exchange Capacity, measure the ability of soil to act as a buffer and allow the exchange of ions. An increase in CEC shows that the soil conditions are increased for biochemical reactions. See Table 6.

TABLE 6

|  | CEC Before (April) | CEC After (June) | % Change |
|---|---|---|---|
| Site 1 | 22.4 | 20.0 | −11% |
| Site 2 | 18.8 | 30.0 | 60% |
| Site 3 | 15.5 | 28.4 | 83% |
| Site 4 | 18.9 | 19.7 | 4% |
| Site 5 | 16.1 | 17.5 | 9% |
|  |  | AVG | 29% |

Example 7

Increased Microbial Diversity

On a test plot in Central Arizona, cantaloupes and garbanzo beans were grown and treated with the composition of Example 1. The microalgae consortium composition was added to water and grown in an open tank, a photobioreactor. Treatment of the soil was continuous at >20,000 cells per mL at 7.5 gal/hour for the whole season of 4 months. The microalgae consortium composition was applied directly into a drip irrigation system.

TABLE 7

| | Trial 1 | | Trial 2 | |
|---|---|---|---|---|
| Parameter | SRD Treated | SRD UnTreated | SRD Treated | SRD UnTreated |
| Heterotrophic Plate Count (Aerobic) | 1.9 | 1.8 | 1.3 | 1.1 |
| Anaerobic Bateria | 1.3 | 1.0 | 0.7 | 0.7 |
| Yeasts and Molds | 1.1 | 1.7 | 1.0 | 0.7 |
| Actinomycetes | 0.5 | 0.6 | 0.5 | 0.6 |
| Pseudomonads | 0.8 | 0.5 | 0.8 | 0.6 |
| Nitrogen Fixing Bacteria | 0.8 | 0.4 | 0.2 | 0.2 |
| Total SRD | 6.4 | 6.0 | 4.5 | 3.9 |

Example 8

Soil Structure

Figure 6A:
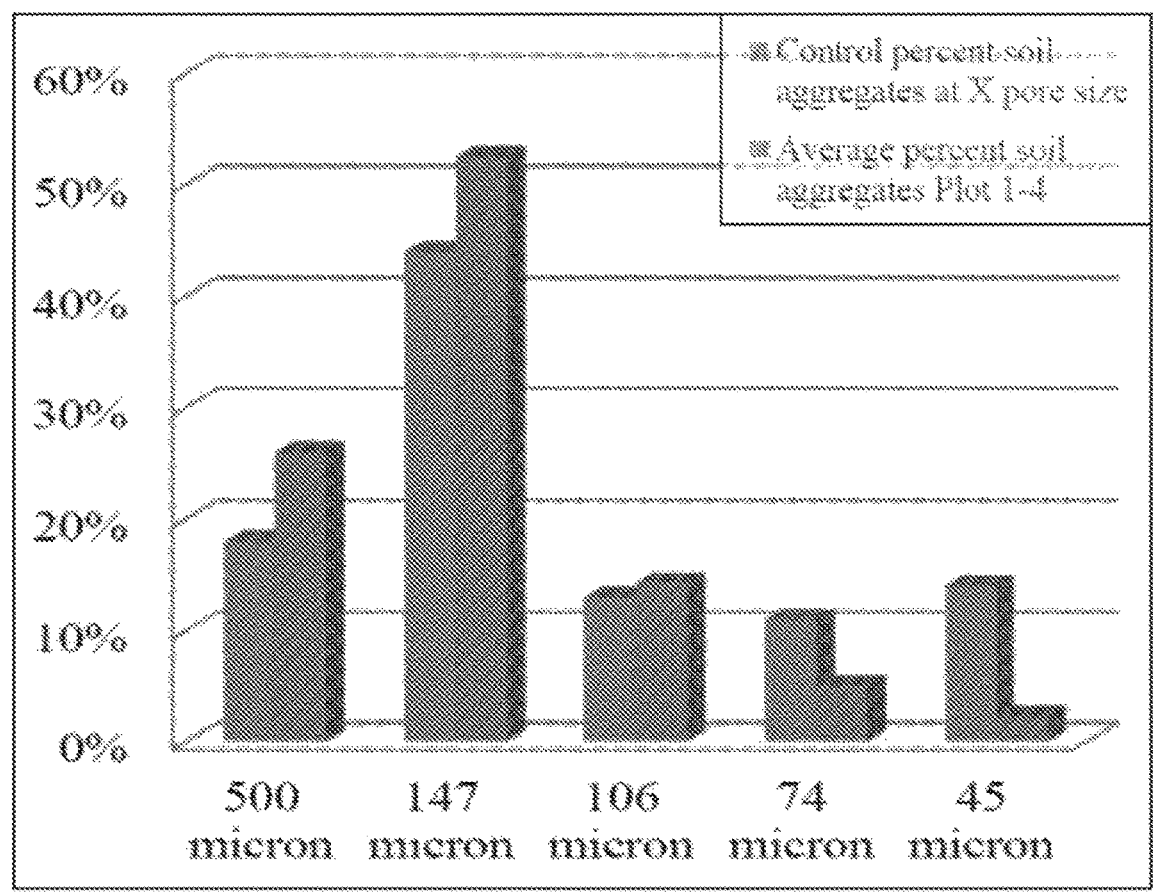
FIGS. 6A and 6B are graphs showing measurements of soil aggregates found after treatment with an exemplary microalgae consortium composition.
Figure 6B:
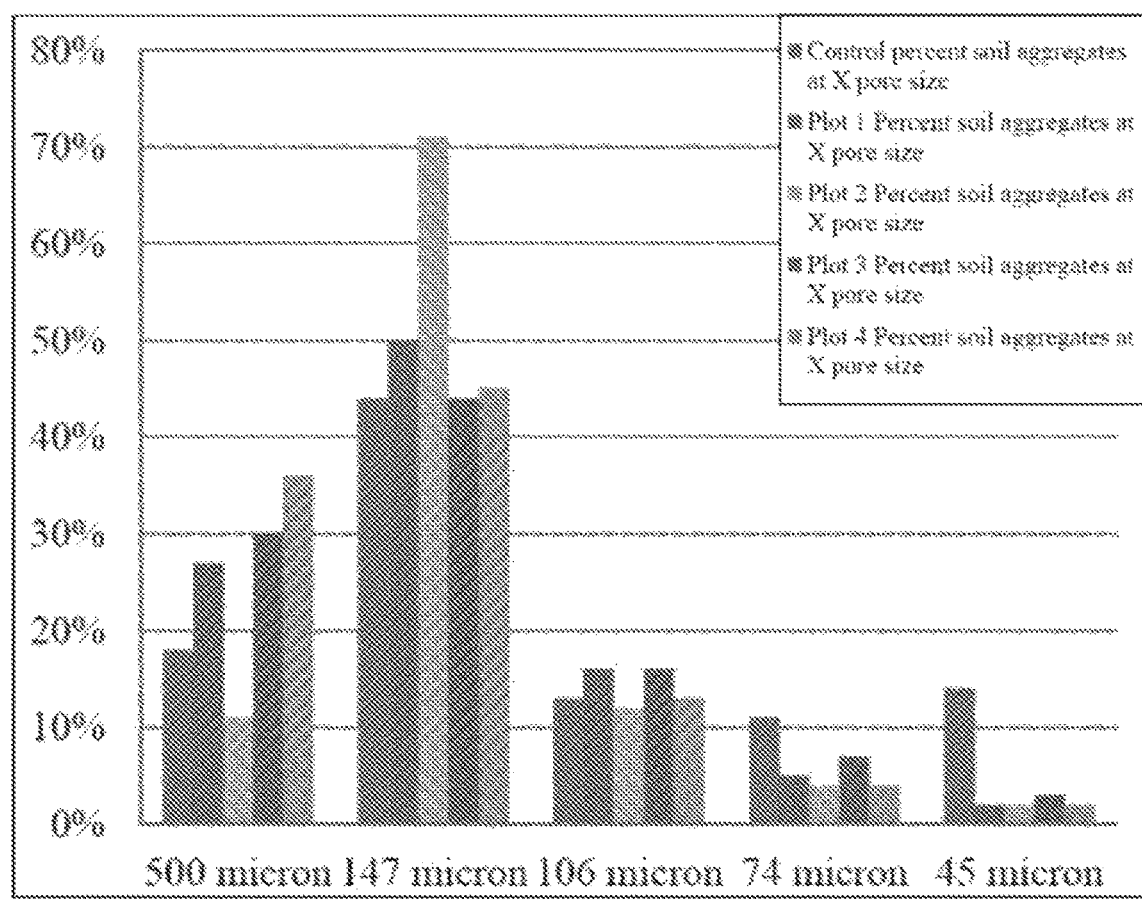

Corn was grown in Yuma, Colo. using a microalgae consortium composition comprising *Scenedesmus dimorphus, Scenedesmus obliquus, Chlorella sorokiniana, Chlorella vulgaris, Cosmocladium perissum, Chlamydomonas sajao, Nannochloris* sp *Micractinium* sp., *Scenedesmus quadricauda*, and *Chlamydomonas moewusii*, at a concentration of at least $10^3$ for each microalgae type. The corn was grown for 5 months as described in Example 1 under conditions shown in Tables 1 and 2. See FIGS. 6A and 6B for graphs showing measurements of soil aggregates found after treatment.

Example 9

Removal of Solid Precipitates from Irrigation Equipment

Irrigation equipment was examined before and after use during application of the composition of Example 1. The microalgae consortium composition is applied at least at a concentration of 1 qt per acre, wherein the quart comprises a microalgae concentration of from about $10^3$ to about $10^6$ cells/mL, and may comprise about $100\times10^6$ cells per qt. It is thought that enzymes present in the microalgae composition catalyze reactions between carbonic acid, sodium bicarbonate and sodium carbonate. Providing a microalgae composition on and/or through irrigation equipment removes precipitates that are present and prevents formation of precipitates on the equipment. Drip irrigation tubing with precipitates is stiff and not flexible as compared to drip irrigation tubing through which a microalgae composition of the present invention has traversed, which are flexible and do not show signs of precipitate formation.

The invention claimed is:

1. A method of solubilizing sodium in soil, comprising:
applying to the soil a microalgae consortium composition comprising *Scenedesmus quadricauda, Nannochloris* sp., *Chlorella vulgaris, Scenedesmus dimorphus, Scenedesmus obliquus*, and *Chlamydomonas moewusii*.

2. The method of claim 1, wherein the microalgae consortium further comprises at least one of *Chlorella sorokiniana, Cosmocladium perissum, Chlamydomonas sajao*, and *Paenibacillus polymyxa*.

3. The method of claim 1, wherein the microalgae consortium is applied to soil before seeds or plants are planted in the soil.

4. The method of claim 1, wherein the microalgae consortium is applied to soil after seeds or plants are planted in the soil.

5. The method of claim 2, wherein the microalgae consortium is applied to soil before seeds or plants are planted in the soil.

6. The method of claim 2, wherein the microalgae consortium is applied to soil after seeds or plants are planted in the soil.

7. The method of claim 1, wherein the concentration of each type of microalgae in the microalgae consortium applied is at least $1\times10^3$ cells/mL.

8. The method of claim 2, wherein the concentration of each type of microalgae in the microalgae consortium applied is at least $1\times10^3$ cells/mL.

9. A method of solubilizing sodium in soil, comprising:
 applying to the soil a microalgae consortium composition comprising *Chlamydomonas moewussii*, *Cosmocladium perissum*, and *Paenibacillus polymyxa*.

10. The method of claim 9, wherein the microalgae consortium further comprises at least one of *Chlamydomonas sajao*, *Chlorella sorokiniana*, *Chlorella vulgaris*, *Scenedesmus obliquus*, *Scenedesmus dimorphus*, *Scenedesmus quadricauda*, and *Nannochloris* sp.

11. The method of claim 9, wherein the microalgae consortium is applied to soil before seeds or plants are planted in the soil.

12. The method of claim 9, wherein the microalgae consortium is applied to soil after seeds or plants are planted in the soil.

13. The method of claim 10, wherein the microalgae consortium is applied to soil before seeds or plants are planted in the soil.

14. The method of claim 10, wherein the microalgae consortium is applied to soil after seeds or plants are planted in the soil.

15. The method of claim 9, wherein the concentration of each type of microalgae in the microalgae consortium applied is at least $1\times10^3$ cells/mL.

16. The method of claim 10, wherein the concentration of each type of microalgae in the microalgae consortium applied is at least $1\times10^3$ cells/mL.

17. A method of increasing cation exchange capacity of a soil, the method comprising:
 applying to the soil a microalgae consortium composition comprising *Chlamydomonas moewussii*, *Cosmocladium perissum*, and *Paenibacillus polymyxa*.

18. The method of claim 17, wherein the microalgae consortium further comprises at least one of *Chlamydomonas sajao*, *Chlorella sorokiniana*, *Chlorella vulgaris*, *Scenedesmus obliquus*, *Scenedesmus dimorphus*, *Scenedesmus quadricauda*, and *Nannochloris* sp.

19. The method of claim 17, wherein the concentration of each type of microalgae in the microalgae consortium applied is at least $1\times10^3$ cells/mL.

* * * * *